United States Patent
Czaja et al.

(10) Patent No.: US 9,968,840 B2
(45) Date of Patent: May 15, 2018

(54) METHOD AND APPARATUS TO PROVIDE HAPTIC AND VISUAL FEEDBACK OF SKIER FOOT MOTION AND FORCES TRANSMITTED TO THE SKI BOOT

(71) Applicants: Stanislaw Czaja, Cardiff, CA (US); Muhammad Afsar, San Diego, CA (US); Andrzej Bachleda-Curus, Zakopane (PL)

(72) Inventors: Stanislaw Czaja, Cardiff, CA (US); Muhammad Afsar, San Diego, CA (US); Andrzej Bachleda-Curus, Zakopane (PL)

(73) Assignee: IPComm, Cardiff, CA (US)

( * ) Notice: Subject to any disclaimer, the term of this patent is extended or adjusted under 35 U.S.C. 154(b) by 78 days.

(21) Appl. No.: 14/747,179

(22) Filed: Jun. 23, 2015

(65) Prior Publication Data
US 2016/0375346 A1    Dec. 29, 2016

(51) Int. Cl.
*A63C 5/03*    (2006.01)
*A43B 5/04*    (2006.01)
(Continued)

(52) U.S. Cl.
CPC ............ *A63C 11/003* (2013.01); *A43B 5/04* (2013.01); *A61B 5/0022* (2013.01); *A61B 5/1036* (2013.01); *A61B 5/11* (2013.01); *A61B 5/1112* (2013.01); *A61B 5/1121* (2013.01); *A61B 5/1124* (2013.01); *A61B 5/6807* (2013.01);
(Continued)

(58) Field of Classification Search
CPC ......... A63C 11/003; A43B 5/04; A43B 69/18; A43B 2071/0636; A43B 2071/0655; A43B 2220/12; A43B 2220/16; A43B 2220/36; A43B 2220/40; A43B 2220/44; A43B 2220/56; A43B 2220/74; A43B 2225/02; A43B 2225/20; A43B 2225/50; A43B 2225/54; G01S 19/42; G06K 9/00342; H04M 1/725
See application file for complete search history.

(56) References Cited

U.S. PATENT DOCUMENTS 6,498,994 B2 * 12/2002 Vock .................... A42B 3/0433
                                                702/141
9,486,669 B2 * 11/2016 Niegowski ........... A43B 3/0005
(Continued)

*Primary Examiner* — Robert J. Utama
*Assistant Examiner* — Lily M Del Valle

(57) ABSTRACT

A system and method to provide haptic and visual feedback of motion of the skier foot and the forces transmitted to the skiboot insole and consequently to the ski/snow interface. This system comprises a motion and force sensors and a haptic actuator embedded in the skiboot insole in communication with a smart-phone based analysis application, configured to calculate insole motion and orientation and the distribution of pressure points inside the skiboot, then to provide haptic feedback to the skier foot instructing on timing and direction of change in the pressure points necessary to achieve optimal turn parameters. Furthermore, analyzed together with GPS coordinates are transmitted by the application to the cloud based server for further processing. Graphical and numerical representation of data is superimposed over a 3D map of a slope which may be viewed on the user smart-phone or on a remote computer terminal.

17 Claims, 17 Drawing Sheets

(51) Int. Cl.
*A63C 11/00* (2006.01)
*A61B 5/11* (2006.01)
*G06F 3/01* (2006.01)
*A61B 5/00* (2006.01)
*A61B 5/103* (2006.01)
*A63B 69/18* (2006.01)
*G06K 9/00* (2006.01)
*A63B 71/06* (2006.01)
*H04M 1/725* (2006.01)

(52) U.S. Cl.
CPC .............. *G06F 3/011* (2013.01); *G06F 3/016* (2013.01); *A61B 2503/10* (2013.01); *A61B 2505/09* (2013.01); *A61B 2560/0223* (2013.01); *A61B 2562/0219* (2013.01); *A61B 2562/0247* (2013.01); *A63B 69/18* (2013.01); *A63B 2071/0636* (2013.01); *A63B 2071/0655* (2013.01); *A63B 2220/12* (2013.01); *A63B 2220/16* (2013.01); *A63B 2220/36* (2013.01); *A63B 2220/40* (2013.01); *A63B 2220/44* (2013.01); *A63B 2220/56* (2013.01); *A63B 2220/74* (2013.01); *A63B 2225/02* (2013.01); *A63B 2225/20* (2013.01); *A63B 2225/50* (2013.01); *A63B 2225/54* (2013.01); *G06K 9/00342* (2013.01); *H04M 1/7253* (2013.01)

(56) References Cited

U.S. PATENT DOCUMENTS

2013/0191034 A1* 7/2013 Weast ..................... G06F 17/00
              702/19
2016/0335913 A1* 11/2016 Grant ................. G09B 19/0038

* cited by examiner

METHOD AND APPARATUS TO PROVIDE HAPTIC AND VISUAL FEEDBACK OF SKIER FOOT MOTION AND FORCES TRANSMITTED TO THE SKI BOOT

FIELD OF THE INVENTION

The present invention relates to the field of visualization of motion and weight distribution inside the ski (or skate) boot for the purpose of monitoring forces projected through the foot to the ski and snow to aid in training and performance evaluation. A gyroscope, accelerometer, magnetometer, pressure and force sensors are embedded into the sole of the ski boot (or ice skating boot), providing measurement of foot rotational and lateral motions in 10-degree of freedom. Furthermore, one or more actuators are embedded in the skiboot insole, providing haptic feedback to the skier foot. The motion and weight distribution vectors are processed by the micro-controller embedded in the boot sole, and the resulting motion matrices are transmitted to the user smart-phone using Bluetooth, or other suitable short range radio interface. Alternatively, the data from motion sensors may be transmitted to the user smart-phone for processing of motion fusion matrices. The results are synchronized to GPS time and coordinates, then after applying appropriate filtering, the results are transmitted to one or more actuators embedded in the boot insole, providing haptic feedback to the user, indicating the timing and the direction of force distribution between feet and inside each skiboot used to execute turn. Results are also transmitted to the remote location ("cloud service") for further processing using smart-phone cellular radio interface. Said processing includes presenting of the foot motion and force distribution in a form of animation and superimposing said data on the 3D maps obtained from GPS coordinates. The post-processed visual and numeric data may then be received from the cloud server by the user smart-phone or by a remote computer terminal. Furthermore, if an accident (fall without recovery over certain period of time and warning cancellation), is detected, an SMS message informing of said accident is sent to the predefined recipients.

BACKGROUND

Currently monitoring of skier/skiing performance relies on few techniques, such as: skier feelings, instructor/coach observations, etc, and some empirical factors, such as: time measurements, post run video analysis, while the safety and comfort depends on decades old ski binding technology, incremental progress in materials and manufacturing technology. Some analytical methods for data collection during the development phase of the ski equipment are in use today, however, most of those techniques are not practical for the every day training of professional or recreational skier, as they require bulky equipment and require large team of highly skilled technicians to operate.

The comfort, safety and pleasure of skiing are highly dependent on the improvement of the user skills. While most beginners may relay initially on lessons and advise from a ski instructor and make initial progress, progress of most intermediate skiers is slow, painful and based on correction of errors, while progress of professionals is correlated directly to the quality and attention of the coach and the quality and duration of training. In the past, some innovation in recording the pressure points projected by the skier foot on the skiboot insoles were introduced in an attempt to analyze bio-mechanics and as an aid in training. However, those devices can only record distribution of pressure and require synchronization with real-time video of the run to provide meaningful information. And as real-time video synchronization is rarely available to the average skiing enthusiast, the benefit of such devices in training is very limited.

In recent years, the use of mobile devices and, in particular, smart-phones proliferated, all provided by the progress in electronics circuit integration. Today's smart-phone besides providing communication over cellular network is equipped with various input/output capabilities, such as wireless PAN (Personal Area Network), and provides significant computing resources. Such computing and communication resources may be integrated with a motion analyzer embedded into replaceable sole of a ski boot (or skate boot), to provide level and quality of feedback suitable for all—from beginners to professionals. A motion analyzer embedded in the ski boot (skate boot) sole communicating with the user smart-phone or a dedicated cellular interface modem, provides capability to visualize the run characteristic values. The run characteristic values may be stored in the "Internet cloud" for post-analysis or displayed in real-time in a remote location. Such system can be used as an aid in instruction, or as a tool in objective determination of athlete performance—i. e. to determine quality of performance by the free-style skier. Such system may operate using any of wireless technology such as: cdma2000, UMTS, WiMax, LTE. LTE-A, etc.

SUMMARY OF THE INVENTION

This invention describes system allowing visualization of skier's (or ice-skater's) foot motion and distribution pressure points inside the skiboot while providing haptic feedback in a real time by embedding miniature micro-mechanical systems (MEMS) and electronics components into the inner sole of the skiboot. The system comprises of: 3-axis accelerometer, 3-axis gyroscope and a 3-axis magnetometer, to provide motion vectors in 9-degree of freedom. In addition, an atmospheric pressure sensor to provide measurement in changes of atmospheric pressure—to record vertical motion, and two or more force-pressure sensors—to record forces applied to the toe and heel of the boot, are added. Such system provides measurement of linear acceleration, rotational vectors and orientation (attitude) in three-dimensional space providing representation of motion. This motion and vectors are synchronized with GPS time and coordinates are sent to a remote location for processing and presentation in visual and numerical form. Such presentation may be used to understand the precise cause—in relation to time/position of the error made by the skier to aid in training and/or provide link to references explaining the nature of error and suggesting remedy. Furthermore, a haptic feedback actuator located under the user's big toe provides feedback (and advise) about changes in distribution of the forces inside each skiboot, which are necessary to execute the desired turn. This feedback is based on the analysis of the current phase of the turn, information about the user and equipment physical parameters and the knowledge of the points on the force of user feet, which must be applied to achieve smooth transition between different phases of the turn. Beside aiding in training, the visual presentation of the athlete's movement in 3D space and/or the topological information, may aid in providing objective assessment of the performance in such disciplines as: free-style skiing, ice skating, etc.

The motion processing system of the present invention comprises motion capture sub-system consisting of: a multiaxis accelerometer, gyroscope and magnetometer (compass), plus a barometric pressure and force sensors; a microprocessor; and a personal area network (PAN) radio interface to communicate motion vectors to the smart-phone based application. According to one embodiment of this invention, said motion sub-system is embedded in a replaceable sole of the ski boot inner-lining, while in another embodiment of this invention, the motion capture sub-system is directly embedded in the ski boot.

It is well known that ski or snowboard turns when moments are applied to the ski edge by skier's body through the forces applied to the skier's foot, and that the turning performance is determined by said forces and the reactions introduced by ski-snow contact. Understanding of skiing bio-mechanics allows determination of proper pressure distribution on the skier's foot in order to make the foot pronate to control the external forces that disturb equilibrium of balance. To establish balance platform, skier must place the center of pressure on the outside (of the turn) foot, and only in specific conditions during the turn. In the foot/skiboot system, the center of pressure (COP), lays at the point where the resulting force ($F_R$) of interaction between the ski and snow acting on a skier at ski between the turns (flat phase of turn), pulls his center of mass (COM) downward towards the snow and is opposed by muscles preventing a fall. Said knowledge may be augmented with real-time tracking of ski boot motion and the distribution of pressure points inside the ski boot during difference phases of turn.

Analyzing motion, one may determine the current phase of the turn and knowing the skier and equipment physical parameters may predict (extrapolate) the desired rate of ski rotation, then provide haptic stimulus indicating time the COP must be transferred form one part of the foot to another part. Such system, comprising motion and pressure sensors embedded in the ski boots and a smart-phone based application may provide real-time feedback to the skier and visual post-run analysis does provide tool in training.

BRIEF DESCRIPTION OF THE DRAWINGS

A better understanding of the present invention can be obtained when the following detailed description of the preferred embodiment is considered in conjunction with the following drawings, in which.

Figure 1:
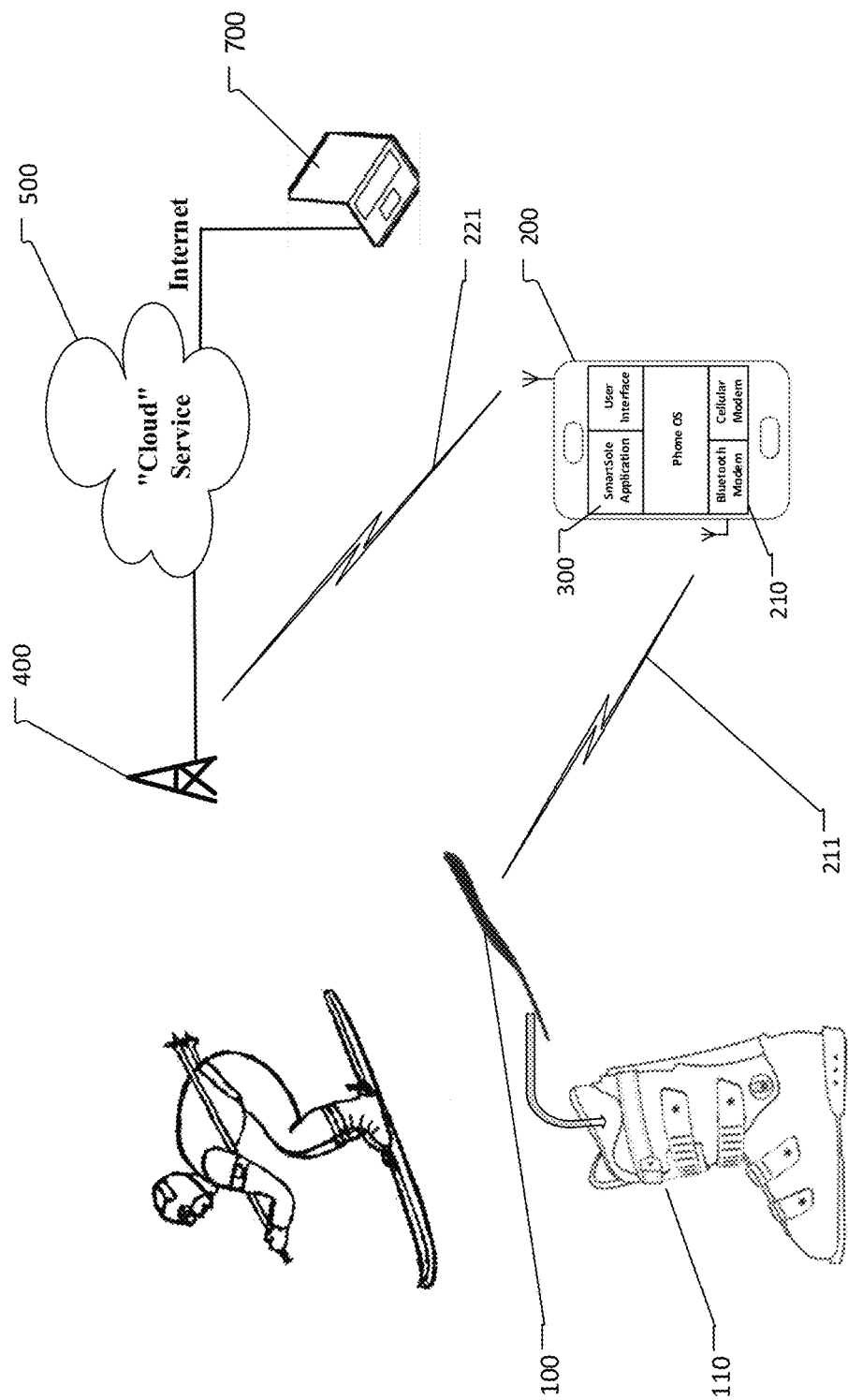
FIG. 1, is an exemplary skiboot haptic feedback system.

While the invention is susceptible to various modifications and alternative forms, specific embodiments thereof are shown by way of example in the drawings and are herein described in detail. It should be understood, however, that the drawings and detailed descriptions are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The following is a glossary of terms used in the present application:

Haptic Feedback System—in the context of this invention is a system able to collect and analyze motion of the skiboot and forces applied by the skier's foot to the sole of the skiboot, then after determination of the phase of the turn, apply a haptic feedback to the skier's foot indicating optimal distribution of the pressure points.

Application—the term "application" is intended to have the full breadth of its ordinary meaning. The term "application" includes 1) a software program, which may be stored in a memory and is executable by a processor or 2) a hardware configuration program useable for configuring a programmable hardware element.

Computer System—any of various types of computing or processing systems, including mobile terminal, personal computer system (PC), mainframe computer system, workstation, network appliance, Internet appliance, personal digital assistant (PDA), television system, grid computing system, or other device or combinations of devices. In general, the term "computer system" can be broadly defined to encompass any device (or combination of devices) having at least one processor that executes instructions from a memory medium.

Mobile Terminal—in the scope of this invention any wireless terminal such as cell-phone, smart-phone, etc. provisioned to operate in the cellular network.

Memory Medium—Any of various types of memory devices or storage devices. The term "memory medium" is intended to include an installation medium, e.g., a CD-ROM, floppy disks, or tape device; a computer system memory or random access memory such as DRAM, DDR RAM, SRAM, EDO RAM, etc.; or a non-volatile memory such as a magnetic media, e.g., a hard drive, or optical storage. The memory medium may comprise other types of memory as well, or combinations thereof. In addition, the memory medium may be located in a first processor in which the programs are executed, or may be located in a second different processor which connects to the first processor over a network, such as wireless PAN or WMAN network or the Internet. In the latter instance, the second processor may provide program instructions to the first processor for execution. The term "memory medium" may include two or more memory mediums which may reside in different locations, e.g., in different processors that are connected over a network.

Near Field Communication (NFC)—in the scope of this invention is a type of radio interface for near communication.

Personal Area Network (PAN)—in the scope of this invention, is a personal are network radio interface such as: Bluetooth, ZigBee, Body Area Network, etc.

Body Area Network (BAN)—in the scope of this invention is a network of sensors attached to the user body communicating over wireless interface.

Motion Monitoring System—in the scope of this invention is a system able to collect various instantaneous vectors such as: acceleration, angular orientation, geo-location and orientation, then using various mathematical operations to provide visual representation of the user's motion.

Ski Equipment—in the context of this invention, is any part of equipment used by the skier, such as: skis, ski boots, ski poles, ski clothing, ski glows, etc.

Equipment Parameters—in the context of this invention, is ski or snowboard design and manufacturing parameters, such as: length, weight, toe/center/tail, stiffness, etc. are extracted after manufacturing and entered into application.

Turn Symmetry—in the context of this invention the level of correlation between pressure levels and locations of the COF applied during the left and right turn.

User Parameters—in the context of this invention, is user's physical parameters, such as: weight, height, skiing competence level, etc. entered by the user into the application using mobile terminal user (UI) interface.

Software Program—the term "software program" is intended to have the full breadth of its ordinary meaning, and includes any type of program instructions, code, script and/or data, or combinations thereof, that may be stored in a memory medium and executed by a processor. Exemplary software programs include programs written in text-based programming languages, such as C, C++, Visual C, Java, assembly language, etc.; graphical programs (programs written in graphical programming languages); assembly language programs; programs that have been compiled to machine language; scripts; and other types of executable software. A software program may comprise two or more software programs that interoperate in some manner.

Topological Information—in the context of this invention, information about the topology of the ski slop obtained through any combination of techniques such as: topography maps, GPS, Radio-Telemetry, barometric pressure monitoring, etc.

User—in the context of this invention, person actively using haptic feedback system.

Center of Pressure (COP)—in the context of this invention is a point location of the vertical ground reaction force vector. It presents a weighted average of all pressures over the surface of the foot that is in contact with the ground.

Center of Mass (COM)—in the context of this invention is a point equivalent of the total body mass in the global reference system and weighted average of the COM of each body segment in 3Dimensional space.

Center of Force (COF)—in the context of this invention a point location of a force applied by skier's foot to the insole surface when the whole ski lies flat and in contact with the snow surface reaction force. Said force location is calculated from pressure data obtained from sensors located inside the skiboot insole and reflect neutral control of ankle muscle.

Cloud Server—in the context of this invention is a computing equipment allowing a client application software to be operated using Internet enable devices.

Accelerometer—in the context of this invention is an inertia based device measuring acceleration component based on device motion and gravity.

Gyroscope—in the context of this invention is a sensor to measure an angular rate of change in device orientation irrespective to gravity.

Magnetometer—in the context of this invention is a sensor to measure magnetic field by computing the angle of the Earth magnetic field and comparing that measurement to the gravity measured by an accelerometer.

Pressure Sensor—Atmospheric—in the context of this invention is a sensor measuring the differential or absolute atmospheric pressure and used to track vertical motion.

Force Sensor—in the context of this invention is a sensor (resistive, capacitive, etc.), used to measure pressure (in Netwons) of a foot on the insole of the skiboot.

Rotation Vector—Angular Velocity—in the context of this invention is a vector quantity whose magnitude is proportional to the amount or speed of a rotation, and whose direction is perpendicular to the plane of that rotation.

Rotation Matrix—in the context of this invention is a matrix that is used to represent rotation in Euclidean space and to describe device orientation.

Gravity—in the context of this invention is Earth's gravity measured in $m/s^2$ and excluding acceleration caused by the user and consisting of a relative angle between device and gravity vector.

Orientation (attitude)—in the context of this invention is an orientation of the device expressed in Euler angles, rotation matrix or quaternion.

Motion Sensor Fusion—in the context of this invention is a method to derive a single estimate of device orientation and position by combining data from multiplicity of sensors.

Global Coordinate System—in the context of this invention is a x/y/z coordination system referenced to the earth magnetic field and in angle of inclination dependent on geographical location.

Local Coordinate System—in the context of this invention is a x/y/z coordinate of the motion sensor located skiboot, where the x-axis is a horizontal and points to the toe of the skiboot, the y-axis is a horizontal and points to the left and the z-axis is vertical and points up.

Euler Angles—in the context of this invention is a three angles introduced by Loenard Euler to describe orientation of a rigid object using sequence of three consecutive rotations.

Quaternion—in the context of this invention is a mathematical expression used to calculate rotation state of the device using the axis and angle of rotation.

DESCRIPTION OF PREFERRED EMBODIMENT

The invention comprises a skiboot (or ice-skate boot) insole configured to measure distribution of forces transmitted to the skiboot insole during run, a 3D motion processing element, a linear resonant actuator to provide feedback to the skier's foot and a wireless personal are network (PAN) transceiver—such as: Bluetooth, ANT, etc., communicating force and motion data to the smart-phone based application. Based on the knowledge of skiing bio-mechanics, and the information received from the skiboot insole, the smart-phone based application predicts the intended ski trajectory, then provides haptic feedback to the foot of the skier, suggesting proper distribution of pressure points on the insole. Furthermore, the smart-phone application transmits the pressure and motion data obtained form the skiboot insole together with the GPS timing and coordinates to the remote location for post-processing using wireless cellular network. During post-processing, a 3D map based on GPS coordinates is retrieved and superimposed on the motion/pressure data, which may be provided in real-time on a remote computer or a smart-phone. Alternatively, post-processed data may be stored on the remote server and retrieved later by the user.

The insole of the present invention comprises several Microelectromechanical (MEMS) motion processor, providing capability of measuring motion in 10-degree of freedom. Said capabilities are enabled by integrating a 3-axis accelerometer, a 3-axis gyroscope, a 3-axis magnetometer (compass), and a barometric pressure sensor, then process the vectors obtained from said sensors by one of well known motion fusion algorithms. In addition, to motion processing, two or more force pressure sensors are also embedded in the sole, said pressure sensors record the force applied to the pressure point on the insole. When the change in distribution-migration of the center of force (COF), is combined with the motion data, we can obtain the phase of the turn the skis are in, then scaling such results by user and equipment information (weight, height, ski side-cut radius, etc.), provide feedback to the skier's foot indicating timing of change and the amount of pressure necessary to obtain desired turn, while recording said pressure, motion and errors.

Most skiers have an intuitive understanding of skiing, gained from practice and understanding some of the physics behind skiing. Such understanding is useful to skiers of all levels, as it identifies key principles, enabling to properly execute certain movements to improve performance. In general, skiing (downhill), involves high speed run down the sloped terrain using quick turns. The skier gains speed by converting gravitational potential energy into kinetic energy of motion, so the more a skier descends down a heel, the faster he goes. A skier maximizes his speed by minimizing resistance to motion, both from air resistance and snow resistance. While the skier minimizes his air resistance (drag) by reducing his projected frontal area, the reduction of snow resistance requires combination of balance and subtle technique of turn. While the turn is essential to go around objects of gates and arrive safely at the bottom of the slope, the turn itself introduces resistance and as such slows the skier. This is particularly pronounced by less experienced skiers, as they skid around their turns and the skis are tilted on their edge and skis plow into the snow. Also, in some cases, a degree of skidding is unavoidable, more advanced skier, will attempt to carve around the turn using skis natural shape (side-cut), and flexibility. To help in "carving the turn", skier will tilt the skis on the inner edge of the turn, and in general, the larger is the angle between the snow and the ski surface, the tighter the turn is. When the ski is flat on the snow, the radius of the carved turn $R_T$ equals the side-cut radius $R_{SC}$, and the ski turns without skid as it travels in the same direction as its velocity.

However, skid is an important technique used to suddenly change direction, slow the speed or even stop. And unlike carving where a skier eases into the turn, a skidded turn is initiated by simultaneously tilting the edge of skis into the snow and pivoting in the direction of the turn. This results in turning in that direction, due to the plowing effect, since the skis are pointed in a direction that is different from the initial velocity. The steering angle determines sharp is the turn, and the loss of velocity. A steering angle of zero results in the skier moving in a straight line with no turning and no slowing down. A steering angle of 90° results in the skier slowing down with no turning, since the force of the snow plowing into skis without sideway component necessary for turn.

By measuring motion of the foot with 9-degree or 10-degree of freedom, one can monitor motion in 3D, then using knowledge of skier and ski physical parameters predict the progress of motion by extrapolation.

In general, downhill skiing comprise straight skiing with a flat skis between two consecutive turns, and the intrinsic skill necessary for skiing is the maintenance of balance. Balance is maintained by the skier's foot, which through numerous joints, tendons, muscles provides receptive field for two main balance metrics—Center of Mass (COM) and Center of Pressure (COP). In this context, the process of skiing may be divided into three phases: $1^{st}$—initiate transition of balance (initiate turn); $2^{nd}$—ski flat (flat ski between turns); $3^{rd}$—pelvic (start next turn). All these phases are initiated and maintained through changes in the distribution of foot COP and application of said pressure to the skiboot through the skiboot insole.

Without much generalization, it is possible to say that the COP during the turn is located on the outside foot of the turn, while during the flat ski phase (between turns), it is distributed evenly between both feet and the net COP lies somewhere between the two feet depending on the relative weight taken by each foot. Furthermore, we may say that the location of COP under each foot is a direct reflection of the neural control of the ankle muscles. The location of COP under each foot is a direct reflection of the neural control of the ankle muscles. Any movement that flexes the foot or toes downward toward the sole (plantar flexion), will move the COP toward back of the foot, while movement of the foot in upward direction (dorsiflaxion), will move COP toward the front of the foot, the movement of foot inward (invertor), moves COP towards the outside of the foot.

The position of COP can be obtained by placing two or more pressure sensors in the skiboot sole, then synchronizing the changes in COP with the motion vectors obtained from the 3D motion monitor. The knowledge of place the COP is at the present time combined with the knowledge of past trajectory, present orientation in 3D space, motion vectors and the location of COP allows prediction of the future ski trajectory. Such trajectory may be changed or influenced by the change in pressure applied to the foot—thus influencing change of COP and in turn change of turn parameters. Such "advise" about the timing and need to change location of COP can be provided through feedback to the skier foot.

This invention describes a system capable of monitoring motion of the skier foot in relation to the snow, measuring the location and distribution of force-pressure point(s), inside the ski boot and provide haptic feedback to the skier's foot, instructing on the time and direction the center of force (COF) must be moved for the optimal execution of the current turn. Such system comprises a skiboot insole for processing of motion and to provide haptic feedback, a smart-phone based monitoring application communicating with the insole using Bluetooth (or other suitable), personal area network (PAN) wireless technology, and with the cloud based server using cellular wireless technology.

The exemplary system is presented in FIG. 1. Here an insole 100, of a ski boot 110, with an insole 100, communicates with a monitoring application 300, hosted in a smart-phone 200. The monitoring application 300 pre-processes the motion and pressure data, retrieves a GPS time and coordinates from the smart-phone and sends said data using smart-phone cellular radio interface 221, to the cloud service 500, for further post-processing, while the pre-processed motion and pressure data are used to provide haptic feedback to the actuator located in the insole. Based on GPS coordinates extracted from data, the cloud server retrieves 3D map of the area, then superimposes the graphical and numerical parameters of the run on said 3D map. This map, together with the graphical and numerical parameters of the run may be displayed on the remote computer or viewed on the user smart-phone.

Figure 2:
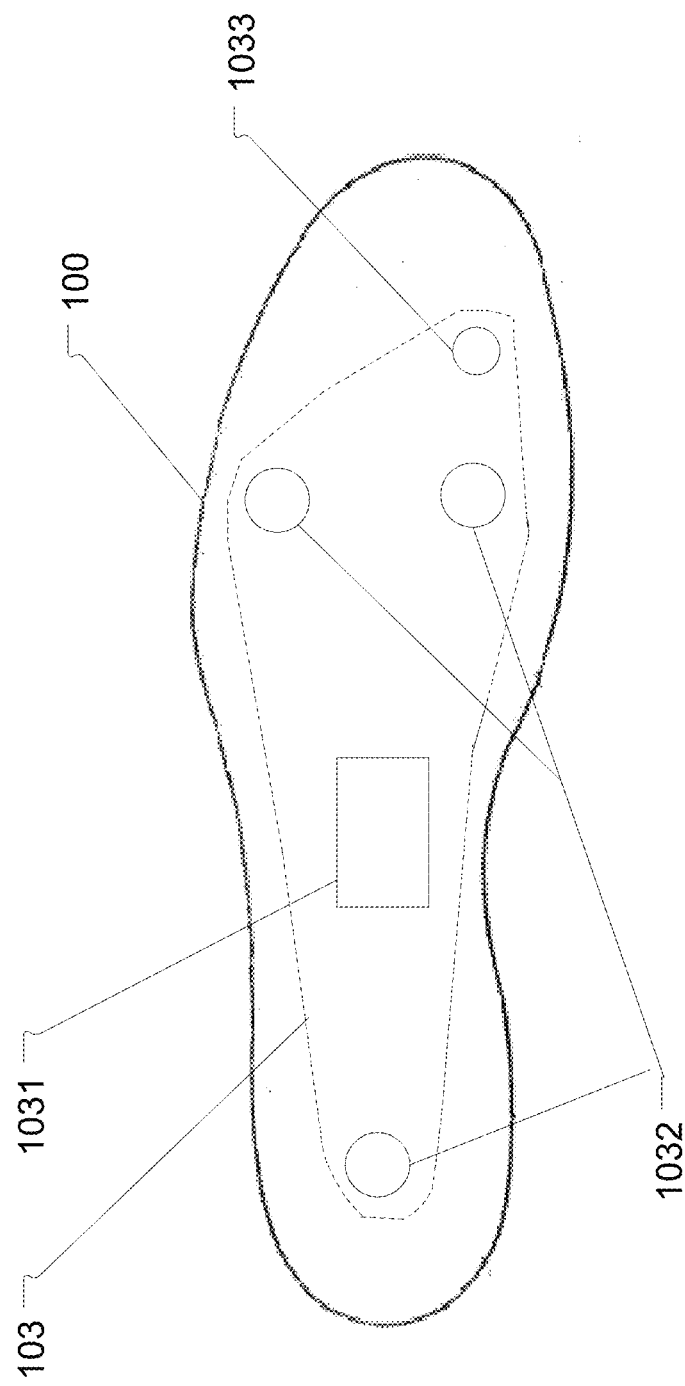
FIG. 2, depicts an innersole and the components of the exemplary haptic feedback system.
Figure 3:
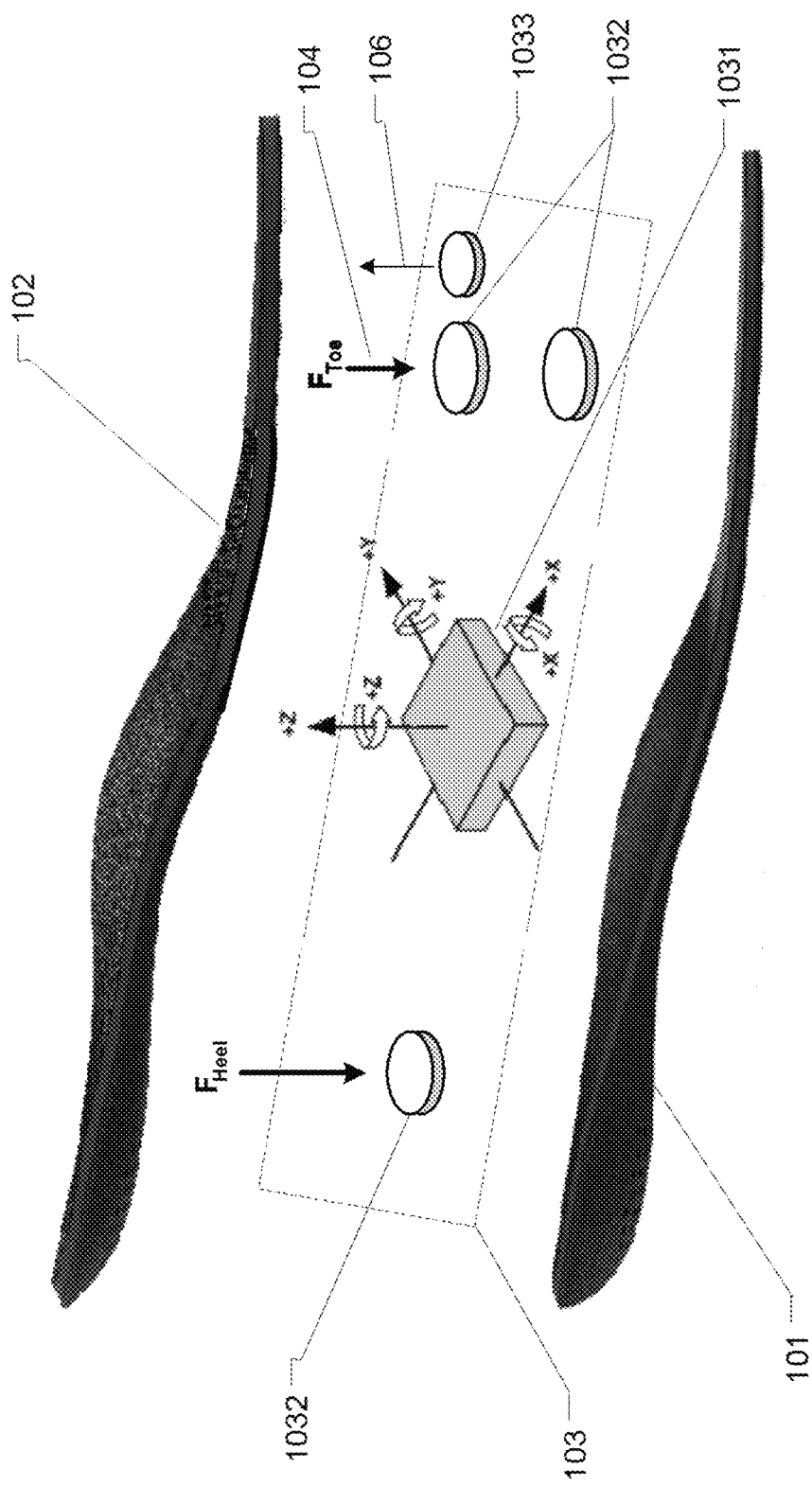
FIG. 3, presents a cross-section of the innersole.

Skiboot insole 100, presented on FIG. 2 and FIG. 3, comprises of a lower 101, and upper 102, insole surfaces and a motion processing and feedback sub-system 103, sandwiched in between insole surfaces. The motion and feedback sub-system consist of a motion processing element 1031, two or more pressure/force sensors 1032, and a haptic actuator 1033. The motion processing element 1031, is configured for analysis of motion with 10-degree of freedom comprising several inertial MEMS sensors: a 3D gyroscope; a 3D accelerometer; a 3D magnetometer (compass); and an atmospheric pressure sensor.

The 3D gyroscope is used to measure angular rate change by the insole in degrees per second, thus allowing measurement of angle, travel and as such, track changes in the insole orientation (pitch, roll and yaw angles). The accelerometer is used to measure acceleration of the insole caused by motion due to gravity in an X, Y, Z coordinate system by computing the measured angle of the device, compared to gravitational force and the results are expressed in m/s$^2$. By integrating acceleration vector a(t) over period of time, we obtain velocity function v(t). The 3D magnetometer measures the earth magnetic field at specific location. By computing the angle of the magnetic field, and comparing that angle to gravity obtained from accelerometer, we are able to determine the orientation of the insole with respect to magnetic North. Beside, sensing the direction of earth magnetic field, magnetometer is used to eliminate drift of gyroscope. Furthermore, the insole motion processing element employs an atmospheric pressure sensor to obtain changes in the altitude and rate of descent by detecting ambient air pressure ($P_{amb}$) according to equation:

$$h_{alt} = (1 - (P_{amb}/10132)^{0.190284}) * 145366.45$$

to track vertical motion.

By observing three-dimensional vector of gravity measured by the accelerometer along with measurements provided by gyroscope, we can determine orientation of the ski (pitch, roll, yaw), while the skier is in motion. Also by subtracting gravity vector form acceleration, we obtain linear acceleration of the ski. The orientation angles describe motion, and are used to provide graphical representation of motion. Furthermore, we derive a rotation vector from results provided by accelerometer, gyroscope and magnetometer. This vector represents a rotation around a specific axis and corresponds to the components of a unit quaternion, which represents yaw, pitch and roll and is used to graphically represent motion of the insole.

The quaternion of the insole (and skiboot), is calculated by, first converting gyroscope angular rate to a quaternion representation:

$$dq(t)/dt = \tfrac{1}{2}\omega(t)*q(t),$$

where ω(t) is the angular rate of motion and q(t) represents normalized quaternion. Then, we convert the accelerometer results from local coordinate system, represented as $A_L$ to global coordinate system, represented as $A_G$, by using previously obtained quaternion as:

$$A_G(t) = q(t)*A_L(t)+q(t)'.$$

Then calculate acceleration quaternion as:

$$qf(t) = [0 A_{Gy}(t) - A_{Gz}(t) 0]*gain$$

which is added as a feedback term to quaternion from gyroscope, then add magnetometer data to the azimuth (yaw) component of the quaternion.

Figure 4:
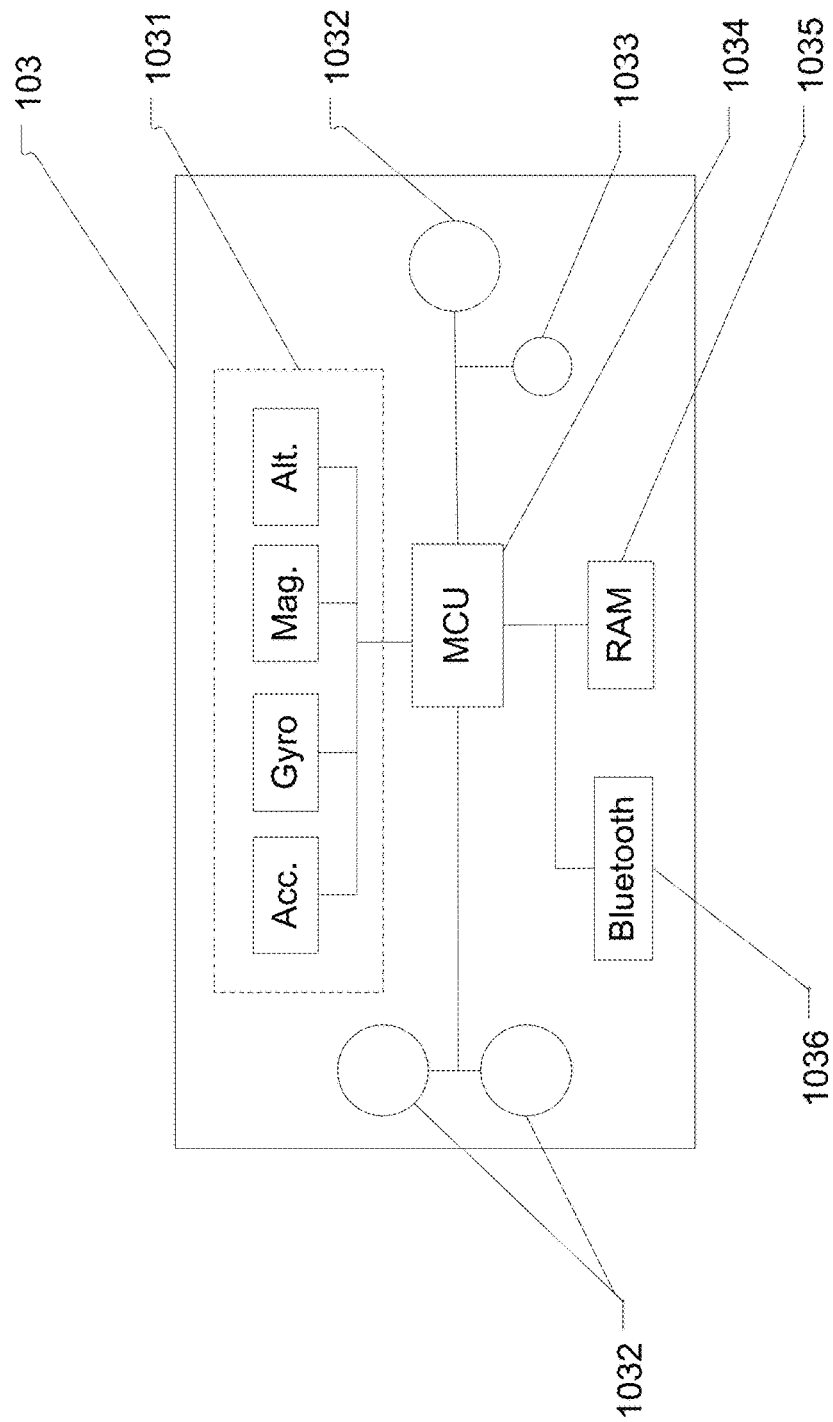
FIG. 4, presents relation between the skier's foot and the components of the skiboot innersole.

The exemplary skiboot insole motion processing and feedback sub-system 103, is presented in FIG. 4, and comprises of: a motion processing element 1031, comprising a 3-axis accelerometer, a 3-axis gyroscope, a 3-axis magnetometer and a barometric pressure sensor. In addition, the motion processing and feedback sub-system consist of several force pressure sensors 1032, a haptic feedback actuator 1033, a Bluetooth RF interface 1036, and microprocessor 1034 with it's program memory 1035. The sensors within the motion processing element 1031, are connected to the microprocessor 1034 using one of appropriate digital interfaces, such as I2C, or an appropriate analog interface. Similarly, the force pressure sensors may be connected to the microprocessor analog-to-digital (ADC) converter using appropriate analog interface or directly to the microprocessor digital interface, while the haptic feedback actuator may be connected to the microprocessor digital-to-analog (DAC) converter.

Figure 5:
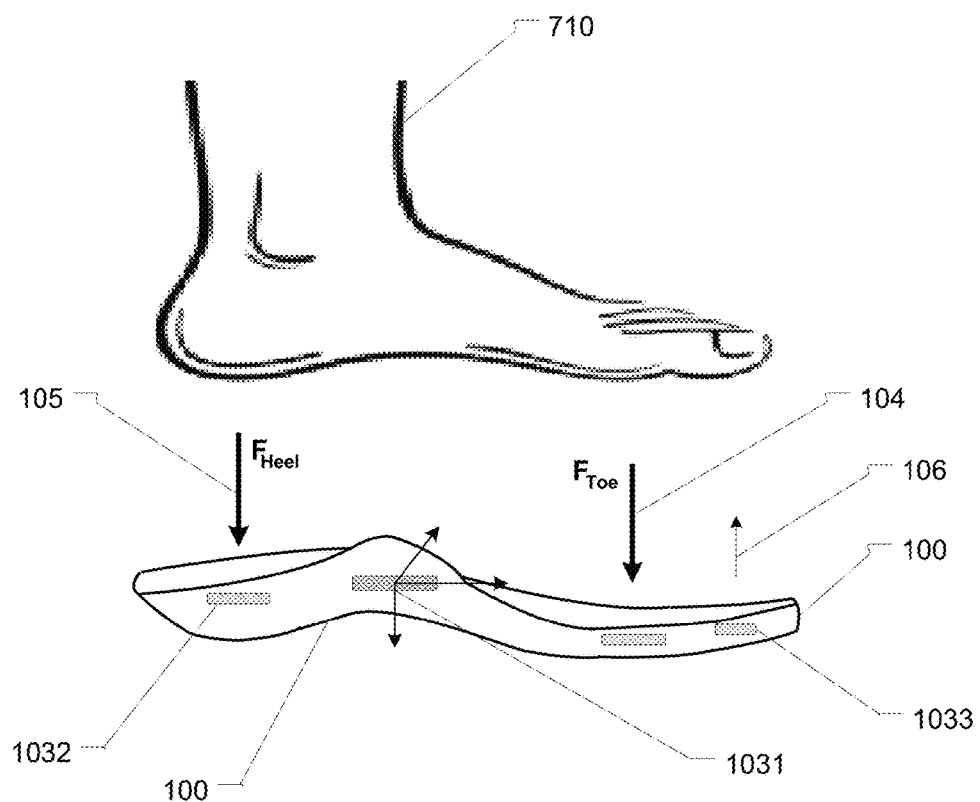
FIG. 5, depicts an exemplary architecture of the haptic system controller.

The relation between skier's foot 710, and the skiboot insole 100, is presented in FIG. 5. During the run, the location of the pressure points to the skiboot/ski and the distribution of pressure (force) between both feet provides the kinetic mechanism necessary to initiate and end a turn. While between turn—frequently referred a 'flat ski', the force is distributed equally between both feet and equally between front and back of the foot, the location of the pressure points between the feet and inside the skiboot changes during the turn. From FIG. 5, one may observe two main location of the force—at the front of the foot ($F_{Toe}$) 104, and the back of the foot ($F_{Heel}$) 105. The actual location of those pressure points and consequently the location of center-of-force (COF) may be measured by two or more force sensors 1032. The haptic feedback 106, to the skier foot is provided by actuator 1033.

Each turn in skiing may be separated into three phases: 1) ski flat phase; 2) start of transition phase; 3) pelvic leg rotation phase. During the ski flat phase, the skier COF is distributed evenly between both skis and located in a neutral point (evenly distributed between toe and heel of the insole). The skier selects inner ski—effectively selecting direction of the turn, and start the transition phase. At this moment, the COF of the inner foot migrates toward the pinky toe and initiated forward movement on the "new" outer ski, this moves the COF of the outer foot toward the big toe. Then enters the third phase by rotating his leg pelvic moving the COF firmly on the outer ski which places the resulting force $F_R$ on the edge of the outer ski.

Figure 6A:
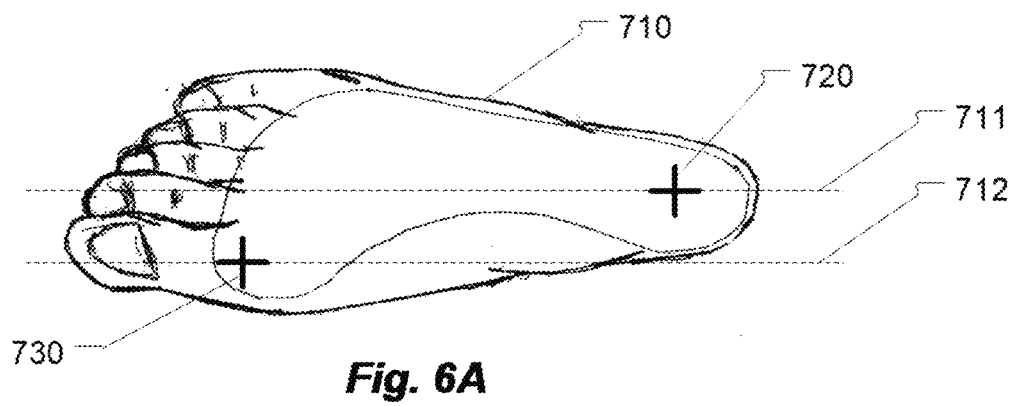
FIG. 6A, presents skier foot bio-mechanical pressure points.

For the outer ski, this process is presented in FIGS. 6A, 6B and 6C and described below. In FIG. 6A, the foot 710, during the flat ski phase between edge change, the pressure is distributed evenly between two main mechanical points 720 located at the heel on the centered axis 711, and on the center of head of the 1$^{st}$ metatestral (MT) bone 730, of a foot and centered along the inside edge 712.

Figure 6B:
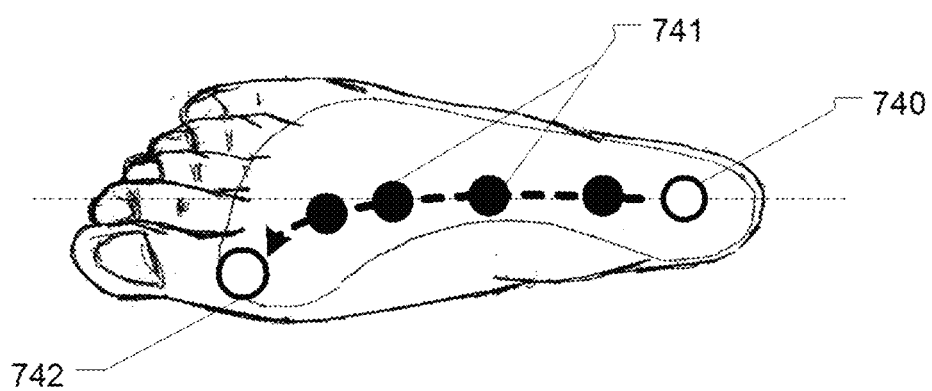
FIG. 6B, presents the center of force (COF) point under the heel and it's forward transition to become center of pressure (COP) in the phase between two consecutive turns.
Figure 6C:
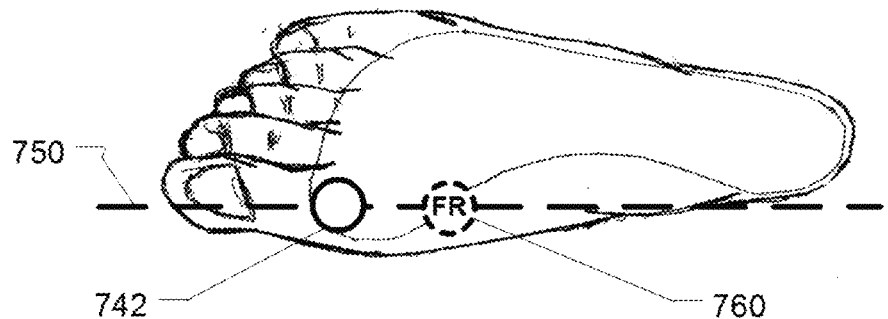
FIG. 6C, presents the COP position at the end of the turn when it lays over the top of the inside ski edge and on the same axis as the center of mass (COM) resulting force ($F_R$)

The start of transition is presented in FIG. 6B, here, when the COF 740 is located under the skier heel and progresses forward to position 742, —the head of the 1$^{st}$ MT. The COF essentially "rolls" inwards, the ankle is plantar flexed and the foot is inverted, the leg rotates while COF moves forward along arc 741, towards the head of the first MT. When the head of the first MT is maximally loaded (FIG. 6C), the COF and the skier fully rest on the outer foot (monopedal stance), while the resulting force $F_R$ 760 align with the COF above the edge of the outer ski 750. At this moment, the rolling of the foot inwards generates torque, which is directed into turn.

Figure 7A:
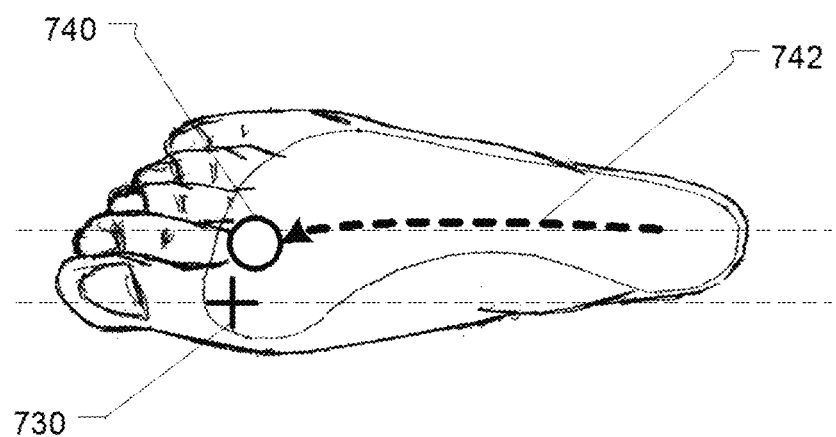
FIG. 7A, presents the incorrect migration of the COF during turn from the foot heel to the head of the second toe.
Figure 7B:
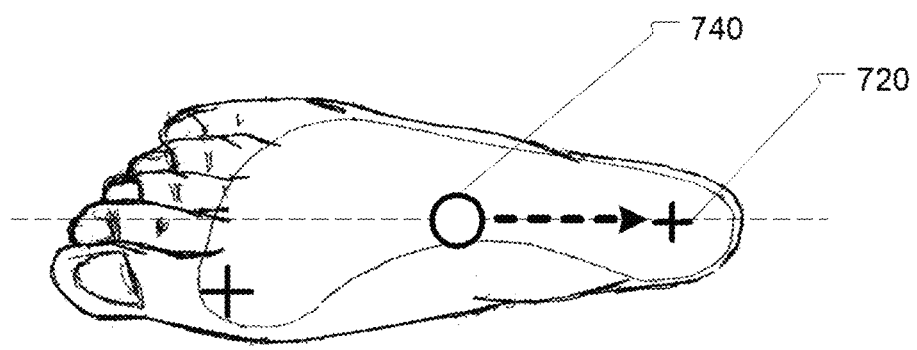
FIG. 7B, presents the migration of the COF back from the incorrectly placed COF to the center of the foot and back to the heel.

When the distribution of pressure between skis or the transition of COF from the heel of the outer foot to the head of 1$^{st}$ MT fails, the turn is unsuccessful and skier looses his balance. The graphical representation of such turn is presented in FIGS. 7A and 7B. At some point between the edge change but before the new outside ski attains significant edge angle (without necessary plantar flex of an ankle), a moment develops between the inside edge of the ski and the COF resulting in inversion moment of force. Torque associated with vertical axial rotation of the leg, FIG. 7B, will reverse the movement of the COF 745, to the point of origin 720 as it is aligned with the heel and lower limb. Such reverse can't be stopped and skier looses his balance.

Figure 8:
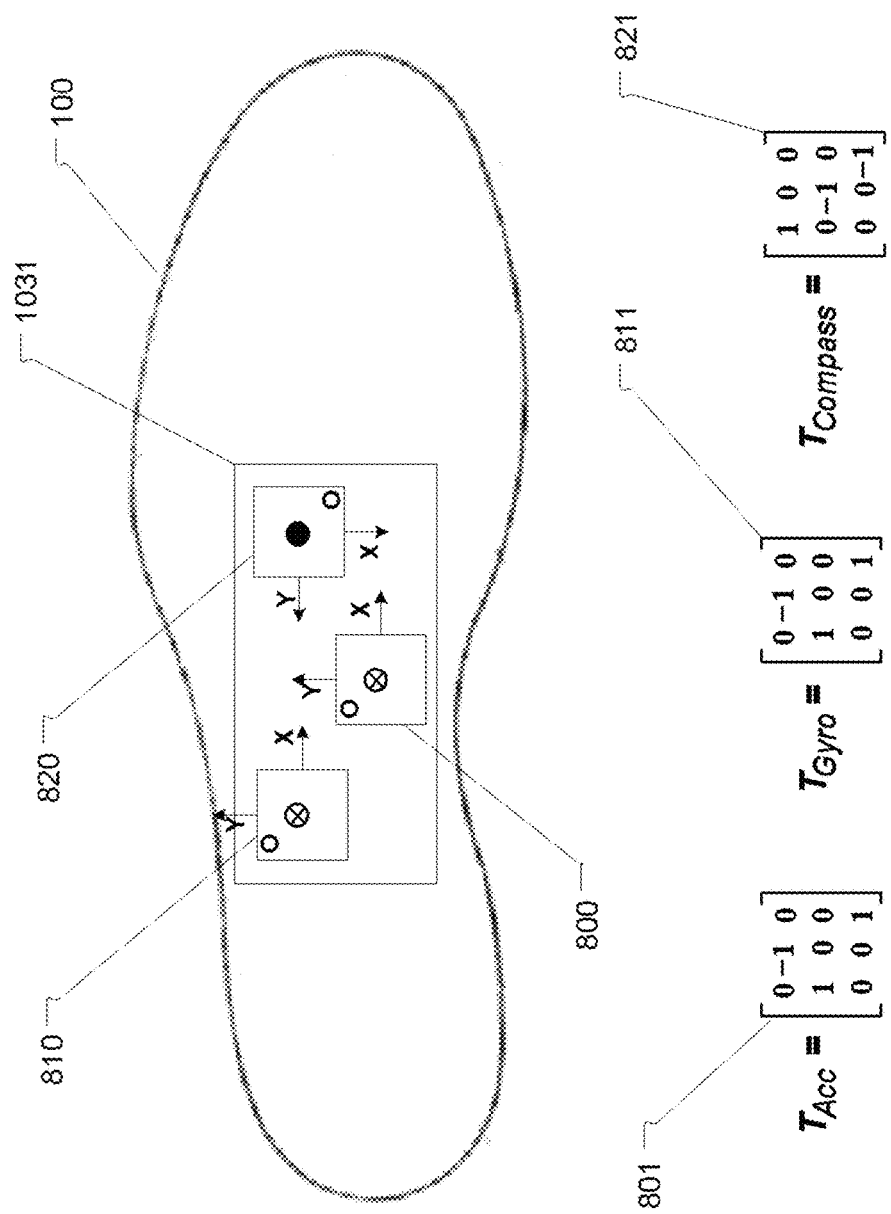
FIG. 8, presents the orientation of the motion sensors (accelerometer, gyroscope, magnetometer), and their transformation matrixes.

An exemplary orientation of motion sensors within the insole and it's relation to their respective matrix is presented in FIG. 8. This relation is important to establish local coordinate system, as the matrix obtained from different sensors will rotate depending on insole orientation in reference to the global coordinate system. The motion processing element 1031, embedded in the skiboot insole 100, and comprises of: 1) an accelerometer 800, which Y axis points to the left side of the insole, the X axis points to the front of the insole and the Z axis points up; 2) a gyroscope 810, which Y axis points to the left side of the insole, the X axis points to the front of the insole and the Z axis points up; and a magnetometer 820, which Y axis points to the back of the insole, the X axis points to the right of the insole and the Z axis points down. Related to this orientation of sensors are respective matrixes: 801, 811 and 812.

Figure 9:
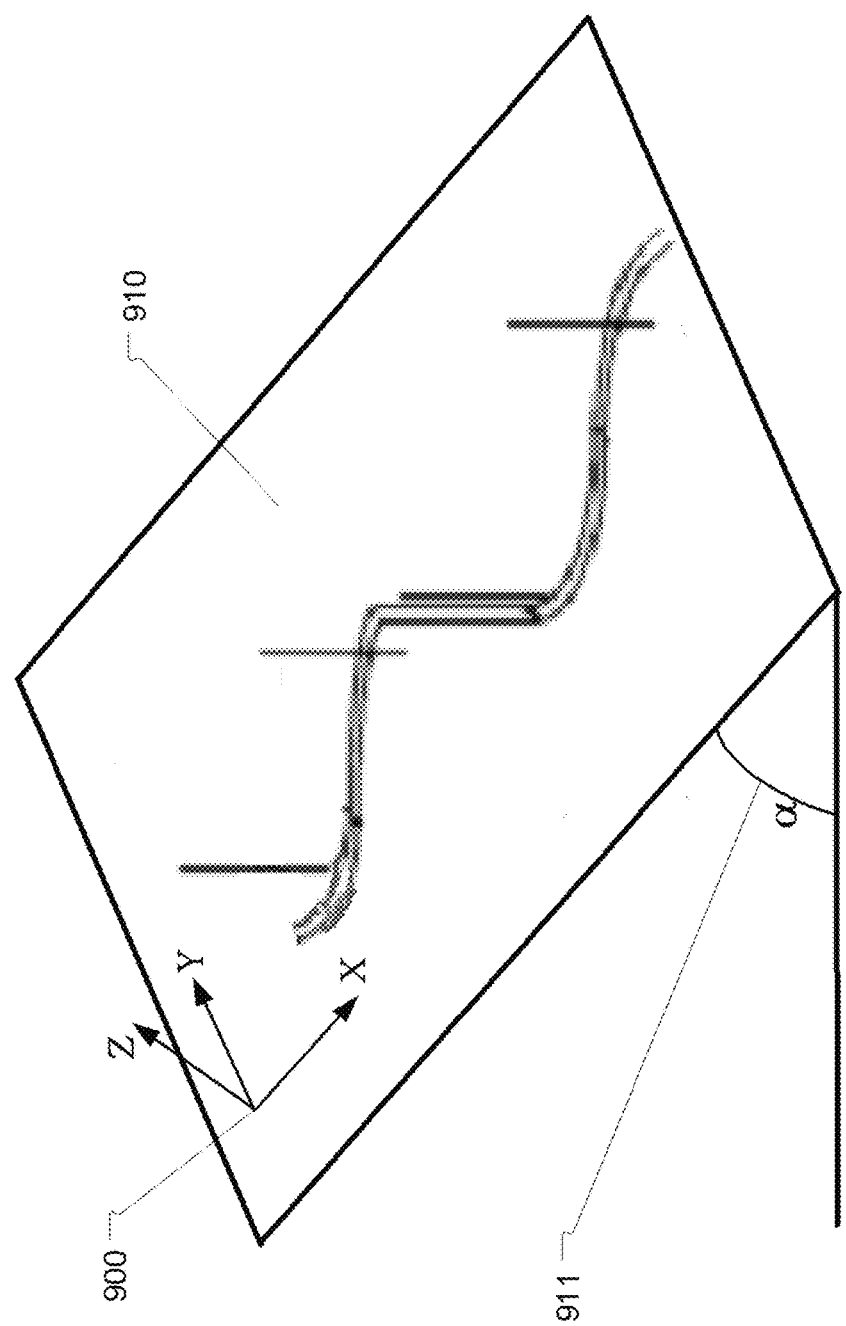
FIG. 9, presents the view of global coordinate system in relation to ski slope.
Figure 10:
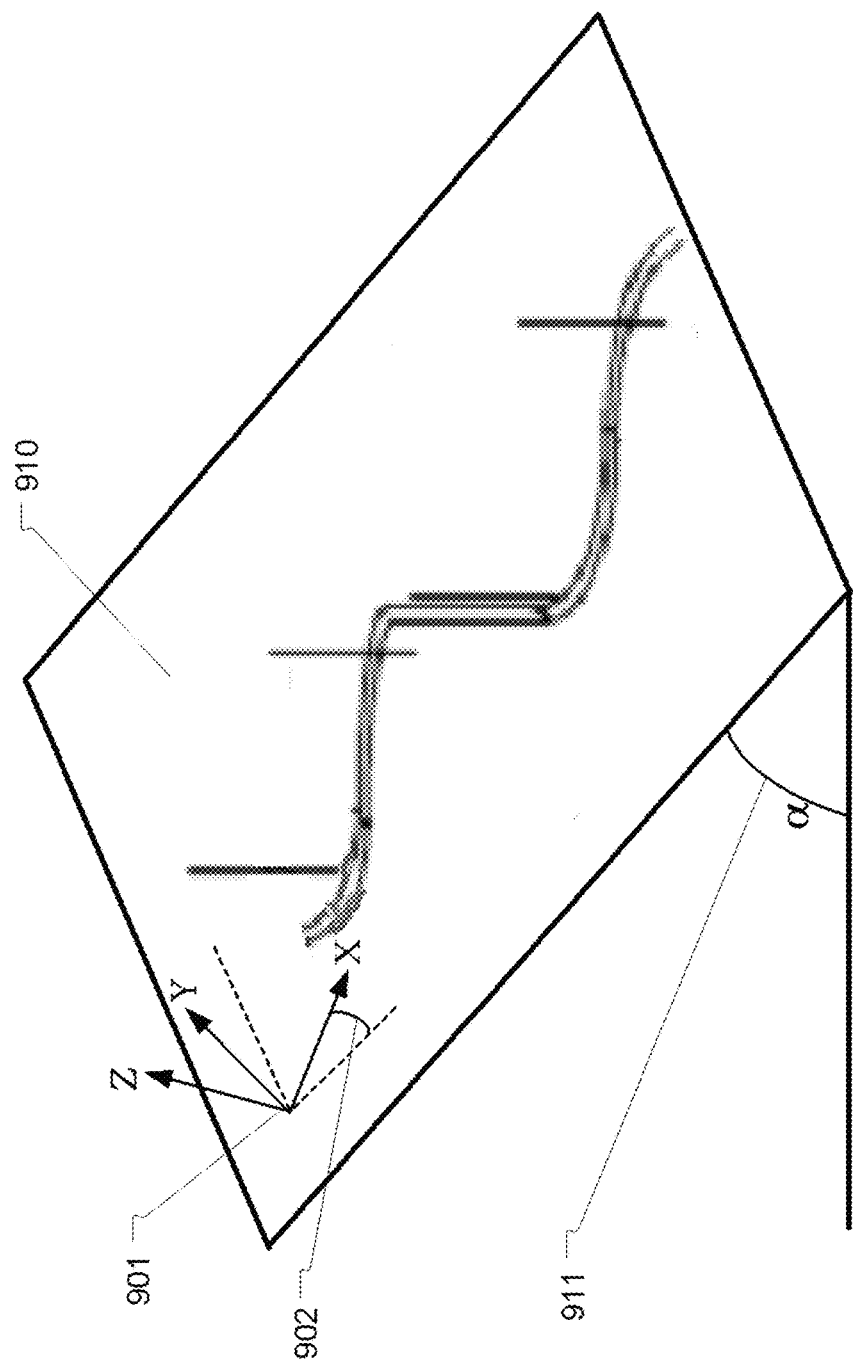
FIG. 10, presents the view of local (skiboot) coordinate system in relation to the ski slope.

The insole global coordinate system is established in reference to the earth magnetic field at the specific geographical location obtained from the magnetometer 820, by comparing it's angle to gravity measured by accelerometer. The orientation of the global coordinate system 900, to the slope 910, with an incline a 911, is presented in the FIG. 9. Here, the Z axis is perpendicular to the ground and the negative Z points in direction of earth gravity. The X axis points to East and the Y axis points to magnetic North. After the global coordinate system is established, the local coordinate system 901 in FIG. 10, a coordinate system of the insole in relation to the global coordinate system may be calculated by reading measurement form accelerometer and gyroscope.

Figure 11:
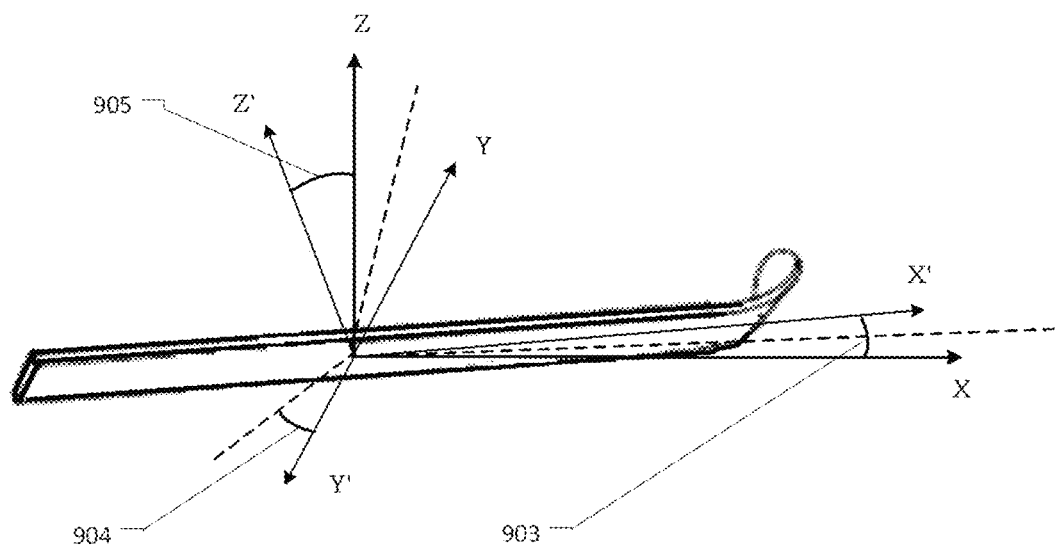
FIG. 11, presents transformation of local coordinate system during turn.

The method of presenting motion and orientation of the insole and by extension ski in the 3D space can be explained based on FIG. 11 and the processing allowing visualization of said motion described in the following sections. Here at time $t_0$, the ski is flat and with the X axis pointing horizontally in the direction of slope line. The Y axis points to the left, while the Z axis point upward. After start of transition, at time $t_1$, ski rotates along the Z axis by angle ψ (yaw), 905, and along the X axis by angle θ (pitch), 903, and along the Y axis by angle Φ (roll), 904, into left turn. This motion may be described in terms of Euler Angles using Euler motion theorem as three consecutive rotations of coordinate system xyz ⇒ x'''y'''z''' ⇒ x''y''z'' ⇒ x'y'z', where the 1$^{st}$ rotation is along the z-axis, 2$^{nd}$ rotation is along the former x-axis and 3$^{rd}$ rotation is along the former y-axis.

The insole orientation may also be described in terms of matrix rotation. For a 3D matrix the rotation θ (pitch), may be described as:

$$R_\theta = \begin{bmatrix} \cos\theta & -\sin\theta & 0 \\ \sin\theta & \cos\theta & 0 \\ 0 & 0 & 1 \end{bmatrix}$$

so the vector $V_0=[1,2,0]^T$ will become $v'=[\cos\theta, \sin\theta, 0]^T$. As the rotation matrix are orthogonal with detriment 1 and with own transpose and an inverse, the rotation matrix will reverse its rotation when multiplied with the rotation inverse. We can also use the matrix rotation to obtain direction of earth gravity in relation to orientation of the insole. When the insole change orientation, its Z axis moves from z to z' by rotation matrix A, according to: $z'=A*z$. As for the local (insole) coordinate system the z' vector is $[0,0,1]^T$, the vector z is obtained by the inverse of rotation matrix.

Rather then use computationally intensive matrix rotation to obtain insole orientation, we may use mathematical expression of quaternion to calculate insole rotation state according to Euler's rotation theorem stating that device orientation may be expressed as rotation about one or more axis. This axis representing unit vector magnitude and angle remains unchanged—except for the sign, which is determined by the sign of the rotation axis represented as three-dimensional unit vector $\hat{e}=[e_y, e_z e_z]^T$, and the angle by a scalar a.

Calculation of quaternion requires only four terms when the axis and angle of rotation is provided. Quaternion extends complex numbers from two-dimensions to four-dimensions by introducing two more roots of −1 as:

$$i^2=j^2=k^2=ijk=-1$$

which are then multiplied with real components as:

$$r+ix+jy+kz$$

then conjugate and normalize to arrive with unity |u|=1, or quaternion.

Figure 12:
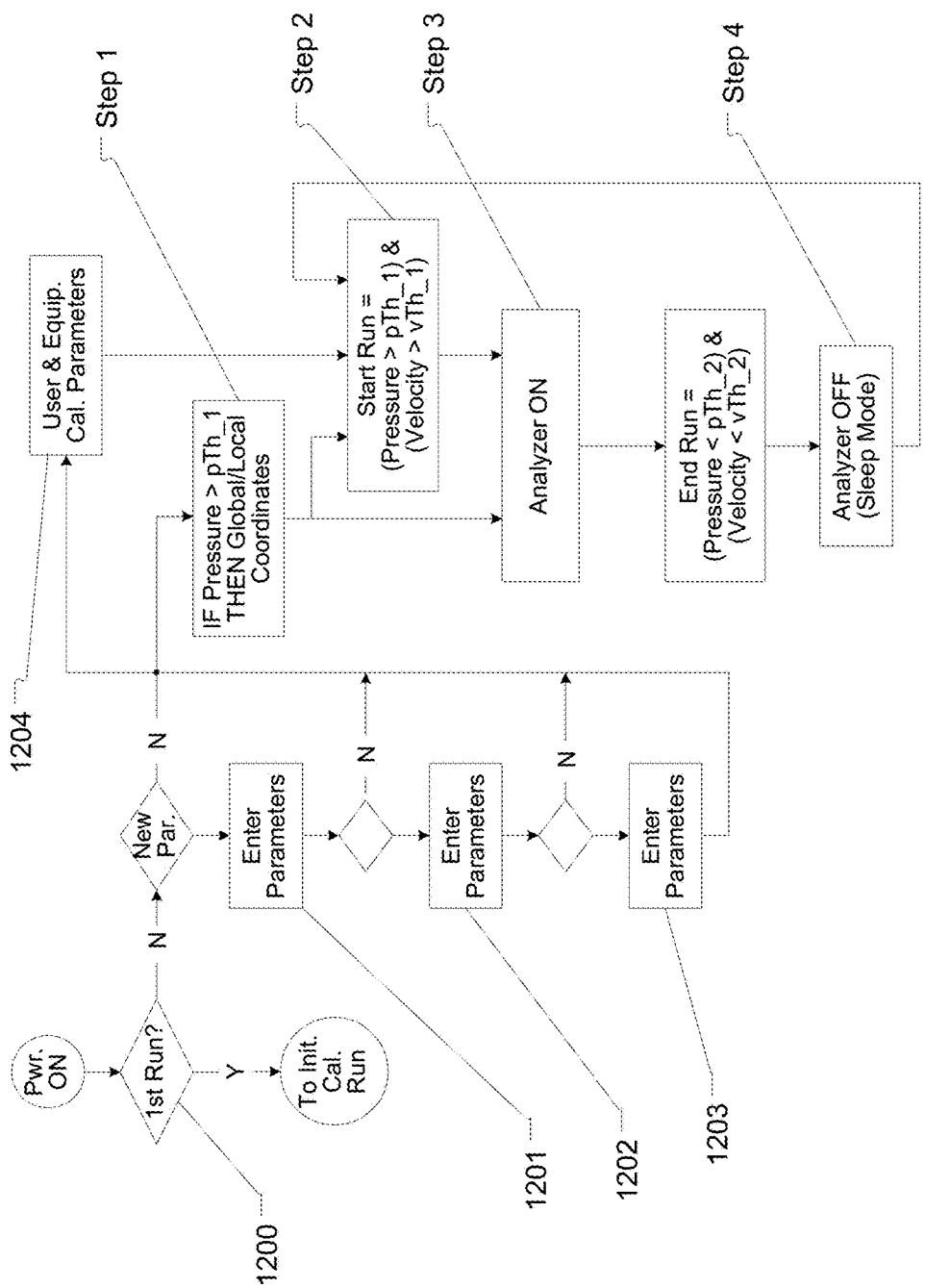
FIG. 12, presents a control process of the haptic feedback system.
Figure 13:
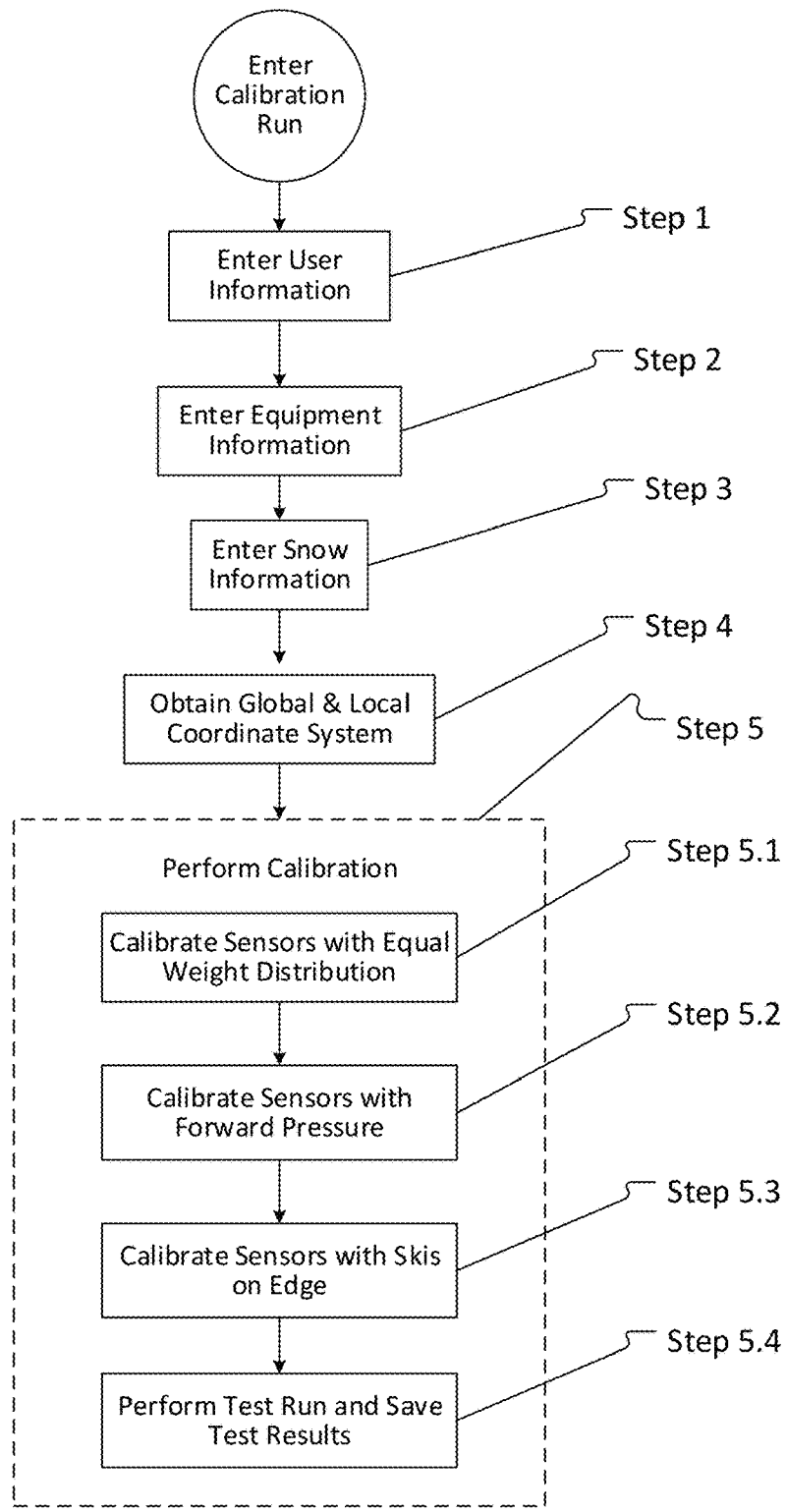
FIG. 13 presents the flow of the haptic system initial calibration.

Operations and procedures of said system is presented in FIGS. 12 and 13 and described in details in the following sections. In FIG. 12, upon initial power-up and association of the insole Bluetooth transceivers with the application, the system control program checks if this is 1$^{st}$ run 1200, indicating the initial calibration procedure was executed. Depending on user parameters, such calibration may be performed during the first run of the day, or at the request by the user, to allow for adjustments to the changing snow conditions, etc. If this is the 1$^{st}$ run, application enters the initial calibration routine of FIG. 13, otherwise, user is given an option to update through the smart-phone user interface (UI), to update one or all system parameters. If said option is rejected, application enters the main control loop, otherwise, the user is prompted to select which information—first (user parameters), second (equipment parameters), or third (snow condition parameters).

The First information 1201, comprises of user parameters consisting among the others: body weight; height; and skiing proficiency level—"beginner", "intermediate", "advanced", "professional".

The Second information 1202, comprises technical parameters of the user equipment, consisting among the others: length of the ski; ski natural turn radius (side-cut); etc.

The Third information 1203, comprises the snow conditions present during the calibration run, such as: "groomed slope", "icy", "powder". This information is used to derive two coefficients—first, to scale the time between the start of transition and when the COF reaches position 742 (FIG. 6B); second, to scale the distribution of COF between inner and outer ski.

The second and third information may be entered by the user manually or scanned to the application from the QR-code or NFC parameter tag attached to the equipment.

The initial calibration procedures comprises of 8 steps which are described in FIG. 13, and in the following paragraphs.

In Step 1, user is instructed to enter his physical parameters, such as weight, which is used to calculate the distribution of force between both skis using Newton's Second Law as well as calculating distribution of force inside the skiboot.

In Step 2, user enters equipment parameters by either scanning a QR-code or a NFC tag attached to the equipment or manually using smart-phone UI. Among the others, some of parameters like the length and the turning radius or, side-cat of the ski are important factors used in conjunction with motion vectors to calculate the ski effective turning and derive an optimal turning radius during turns.

In Step 3, user enters the current snow condition of the slope. This is used to appropriate scale the pressure point (weight) distribution and timing of COF change in different condition of the slope, for example change of technique between powder skiing and skiing on icy snow.

In Step 4, application instructs the user to step into the skis and reads data from motion sensors for the purpose of establishing global and local coordinate system, then in Step 5 instructs the user to perform several exercises:
1) Stand in normal, relaxed bi-pedal position with body weight equally distributed between both skis, then record the force [N], measured by each pressure force sensor;
2) Stand in a crouching position, leaning forward and elbows resting on the knees, then record the force [N], measured by each pressure force sensor;
3) With both skis parallel and without support of the ski poll, bend knees and push inward (as during sharp turn with both skis on the edge), then record the force [N], measured by each pressure force sensor;
4) Instruct user to make a run consisting at least four carved turns. Allow for the ski to accelerate by ignoring first two turn, then record motion parameters during two consecutive turns;
5) End calibration procedure.

After power ON, the MCU 1034, enters standby mode and remains in said mode until an interrupt from the insole pressure sensor is above threshold pTh_1, indicating both of user feet are in the skiboot and on the ground. If new calibration is not required, system enters normal operation, FIG. 12, Step 1, obtains global and local coordinate system, then enters Step 2. In Step 2, system starts monitoring motion, and if the velocity exceeds threshold vTh_1, indicating start of the run, enters into Step 3, then start sending motion and forces data to the smart-phone application over radio interface 211. System remains in State 3, until velocity of the system is above threshold vTh_2 and the pressure force measurement is above threshold pTh_2. When the velocity is below threshold vTh_2 and pressure forces is below threshold pTh_2, indicating end of day (skiboot off), or time-brake in skiing (lift, rest, etc.), system enters Step 4, stops processing of motion and forces, forces radio interface transceiver 1036, into power OFF mode and MCU 1034, into a standby mode—thus conserving power consumption of the system. After exiting Step 4, system remains in the sleep mode until condition of Step 2—pressure force above pTh_1 and velocity above vTh_1 conditions are not satisfied.

The motion and pressure force data received from the insole 100, by the smart-phone 200, is processed by application 300 to provide user with the haptic feedback. Based on signal from sensors, using inertia navigation algorithms, application calculates kinematics of the ski trajectory. Then using user parameters, creates biomechanical model of foot/ski interface, and the sensor kinematics is translated to segments kinematics by measuring the position (and timing) of COF. Such calculation provides two results: one, current ski trajectory; two, prediction of future trajectory in relation to the local coordinate system and location of COF. The first set of results are sent to the cloud based server 500 for further processing using smart-phone cellular radio interface 221, while the second sets of results is used to provide corrective feedback to the user foot.

This corrective feedback is in form of haptic pulses applied by the haptic actuator to the big toe of the foot. This feedback provides information of timing, direction and destination of the COF necessary to successfully start and finish turn. This feedback may be coded in various ways, for example, different frequency and/or force during different phases on turn, etc.

Figure 17:
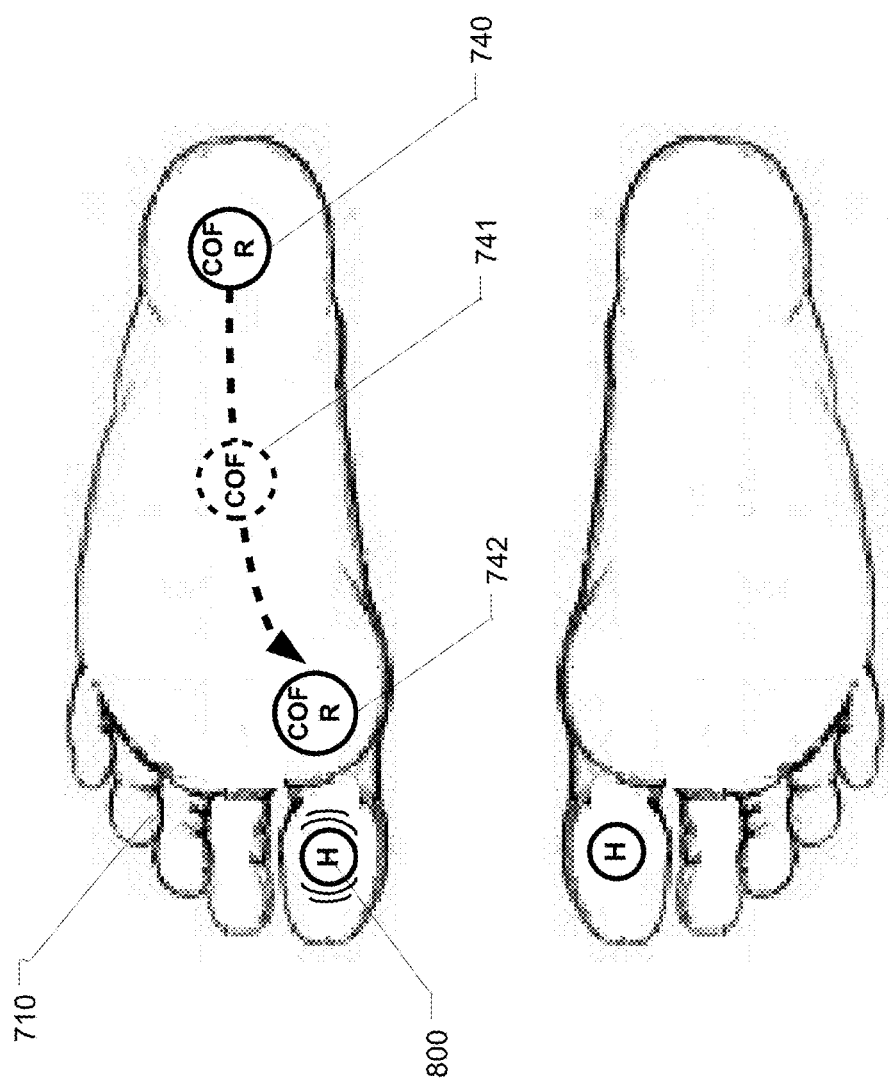
FIG. 17, presents operation of haptic feedback actuator on the outside foot during the transition into left turn.

Operation of said haptic feedback is presented in FIG. 17. Here we see the outside (of the turn) foot 710, right after start of transition, which the haptic feedback actuator 800, vibrating at high frequency (or force), when the COF is still located under skier heel, indicating time to transition on the outside ski and move COF to the base of $1^{st}$ MT. The vibration frequency may decrease while COF moves forward to new position 741, and completely stop when the COF reaches the desired position 742, while never stop vibrating at high frequency when the COF fails to reach the base of $1^{st}$ MT.

Together with the first set of results, application sends to the cloud server GPS coordinates and timing. The first set of data is then used to generate a numerical and graphical presentation of the run. An exemplary representation of run data is presented in FIGS. 14, 15 and 16. Such run data may be retrieved form the cloud server later by the user and displayed on the user smart-phone (for example during the travel on the lift), or in real-time on a remote computer. Furthermore, using the GPS coordinates, cloud server may superimpose said data on 3D map of the terrain, giving additional reference and meaning to the data.

Figure 14:
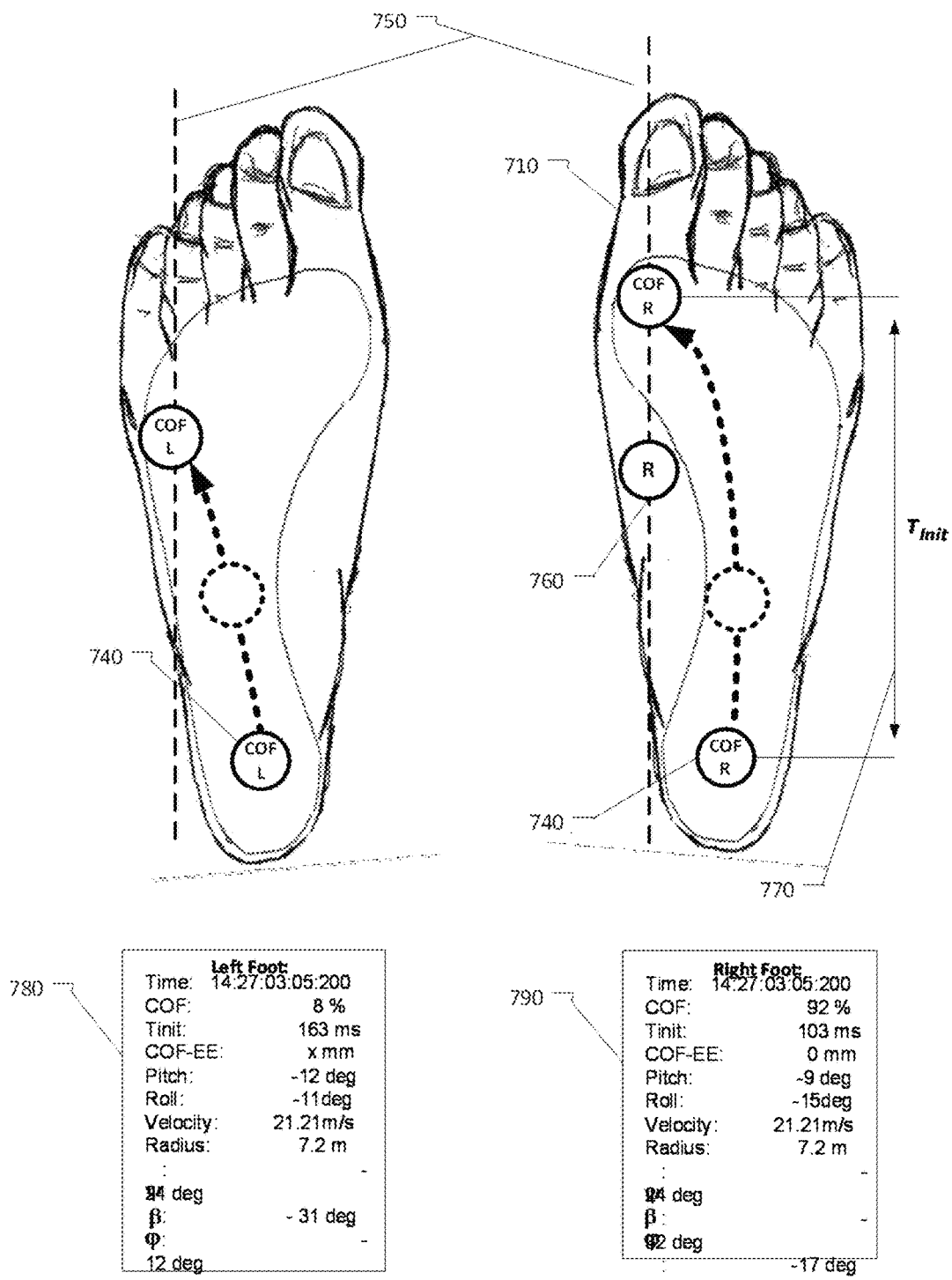
FIG. 14, presents graphical and numerical representation of motion and pressure points transmitted to the skiboot insole by the foot during a successful turn.

After the post-processing of first set of results by the remote cloud server, visual and numerical representation of the run can be displayed on a remote computer or on a smart-phone. Among the others visual presentation possible, some of the visual options are presented in FIGS. 14, 15 *a* 16. FIG. 14, shows left and right foot with a graphical representation of the location of COF and 3D motion parameters in relation to the GPS time. Here we see the movement of the COF 740 from the start of transition into the left turn, the location of the COF 742 after the initial phase of the turn and the time (in milliseconds), of the transition 770. Furthermore, the calculated location of the resulting force $F_R$ 760, a point where the skier center of mass (COM) is acting on the ski and snow.

Figure 15:
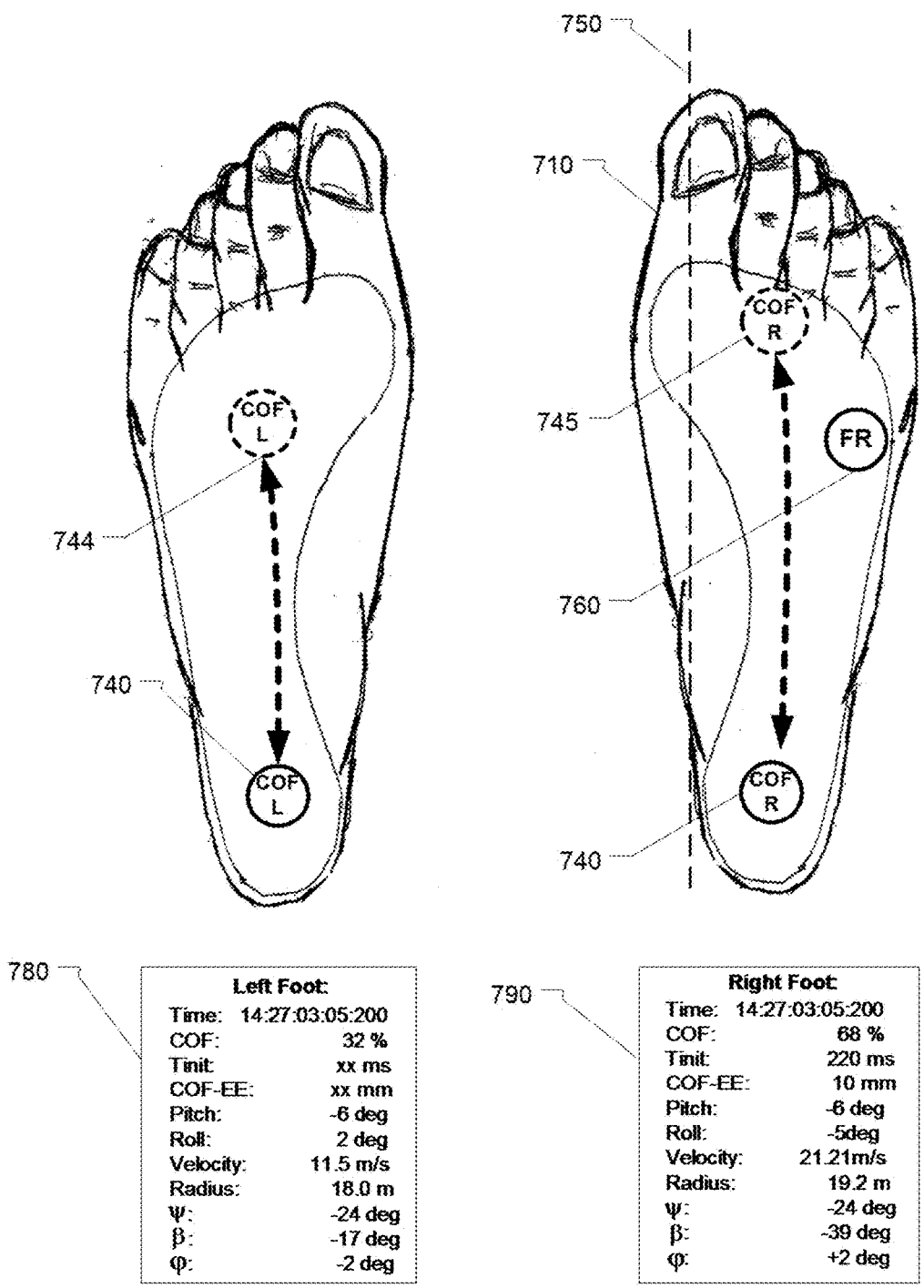
FIG. 15, presents graphical and numerical representation of motion and pressure points transmitted to the skiboot insole by the foot during an unsuccessful turn.

The graphical and numerical results, representing unsuccessful turn is presented in FIG. 15. Here we see the mistake user makes during the start of transition (flat ski=>select new ski=>COF of inner foot to head of $5^{th}$ MT), inner foot COF forward to the center of foot 744. In order to maintain balance the COF of the outer foot was placed between $2^{nd}$ $3^{rd}$ MT 745, and the resulting force moved to the outer edge of the outer foot. In this position the body kinematics does not allow for pelvic rotation and in effect, the COF return to the heels of the feet—balance is lost, turn can't be finished until balance is recovered during next flat ski.

Data are analyzed in relation to velocity, pitch and roll and effective radius of the turn and other numerical results 780 and 790 for left/right foot respectively, and may be used by both the amateurs to improve their skills, professionals during training, judges in analyzing performance of a free style or figure skating competition or even commentators during televised sports events. Furthermore, those results may be sorted and presented in various statistical formats selected by the viewer. An example of such statistical analysis may be use in training and evaluation of turn symmetry—one of most important parameter of measuring progress of a professional skier. Turn symmetry, is term used to describe a pressure applied during the left and right turn. The closer is the distribution of pressures between inner/outer ski during the left and right turns, the better will the skier perform. Such analysis is currently limited to visual observation by the coach of the racer during a run over a specific part of the slope where the transversal angle of the slope maintains relatively constant angle to the line of the slope. Such observation is subjective, prone to errors and of limited value—as it's impossible to evaluate the symmetry of pressure visually and specifically on the slope with changing topographical parameters.

Turn symmetry statistics can be performed as follows:

Log all left turns into LEFT_SET, and all right turns into RIGHT SET;

FOR each turn with $\Phi_L = \Phi_R$ OR $-\Phi_L = +\Phi_R$ OR $+\Phi_L = -\Phi_R$ (roll);

Extract pressure points and force data;

Sort pressure points and force data in the descending order of difference.

Similar method may be used for numerous other parameters of the run.

Figure 16:
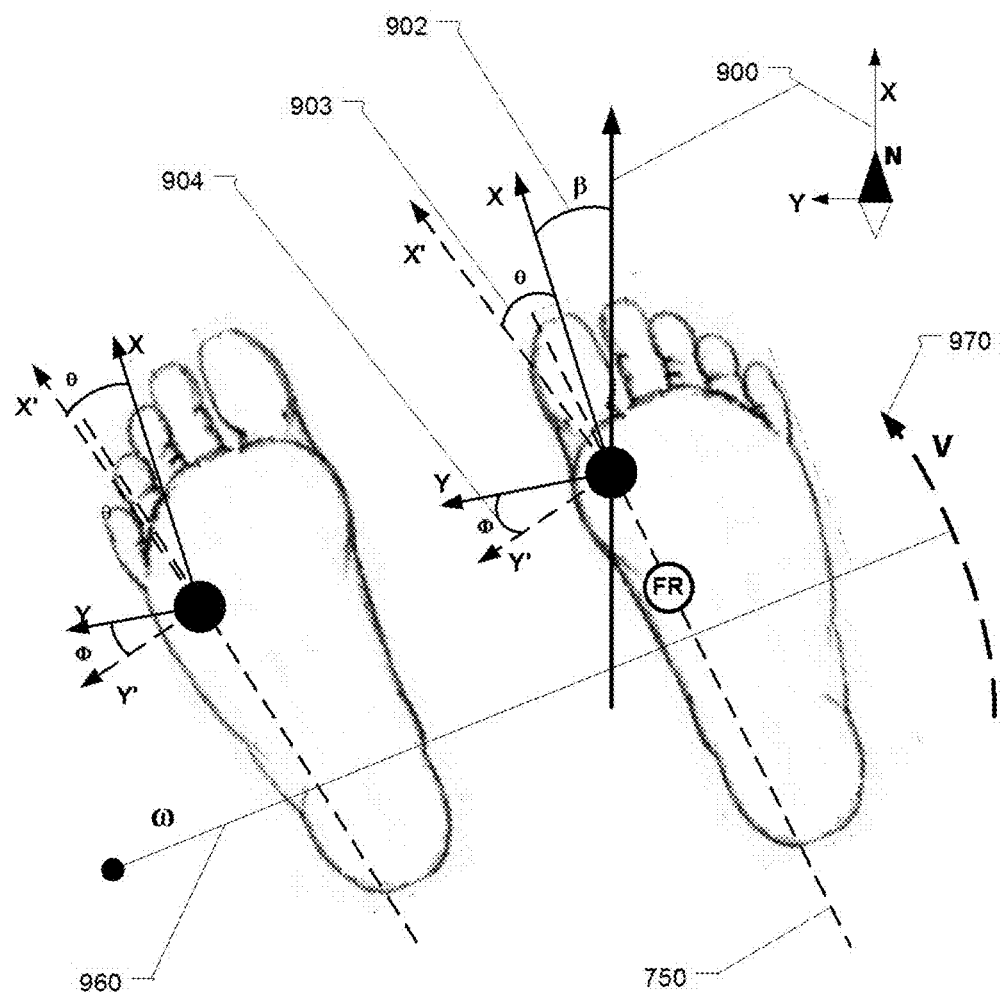
FIG. 16, presents another version of graphical representation of motion in relation to the pressure points on the skiboot insole.

Different view of the data presented in FIG. 16, where both feet are shown in relation to the global coordinate 900, the angle β, 902 to the local coordinate X, pitch Θ, 903, of the ski (angle between X and X)', the roll inside the turn Φ, 904, the effective turning radius ω, 960, and velocity V 970. The location of resulting force $F_R$ in relation to the ski edge 750 is also presented.

Another embodiment of feedback system may employ direct control by an instructor of coach. Here, motion and force sensors data is relayed by the smart-phone 200, to the remote device 700, operated by instructor or coach, who maintains visual contact with the user. On the device 700, data is processed by application 300, enhanced with a user interface (UI), allowing to manually control the haptic feedback actuator embedded in the user skiboot insole. The input from the terminal 700, UI operated by instructor, is send back over wireless cellular interface 400 and 221, to the user smart-phone 200 and then using the PAN wireless interface 210 to the haptic feedback actuator 1033, located in insole 100. Such embodiment allows the couch to directly influence the user actions and tailor his training/progress according to predefined plan or changing slope conditions.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes", "has" or "having" are used in either the detailed description or the claims, such terms are intended to be inclusive in a manner similar to the term "comprising" as "comprising" is interpreted when employed as a transitional word in a claim.

It is understood that the specific order or hierarchy of steps in the processes disclosed is an example of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented Those of skill in the art would understand that information and signals may be represented using any of a variety of different technologies and techniques. For example, data, instructions, commands, information, signals, symbols, etc. may be referenced throughout the above description by other means.

Those of skill would further appreciate that the various illustrative logical blocks, modules, and algorithmic steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

We claim:

1. A system to analyze motion and balance of a skier by analyzing location of Center of Pressure (COP), and timing of the COP location change, and changes in location and distribution of Center of Force (COF) applied to ski boot insoles, and using said analysis to provide estimation of location of the skier Center of Mass (COM), and ski trajectory and to provide instructions to the skier on location the COP must be applied, wherein said system comprises:
   motion and force processing element embedded in a ski boot;
   haptic feedback actuator embedded in the ski boot; and
   a smart-phone based analysis application in communication with the motion and force processing element using wireless radio interface,
and wherein the motion and force processing elements are configured to estimate three-dimensional motion vectors and change a of location and value of COP and the COF, and wherein said estimate of motion vectors and first information provides estimates of the skier's Center of Mass (COM), and wherein said estimate of motion and second information provides estimates of the ski's trajectory, and wherein the smart-phone based analysis application is configured to:
 obtain the skier's location GPS coordinates;
 store the motion vectors, location and values of the COP, COF and COM and the GPS location coordinates;
 integrate changes in motion vectors into a three-dimensional representation of the skis' trajectory;
 transmit the vectors, location and value of the COP, COF, COM and GPS location coordinates to a remote server as third information using the smart-phone cellular radio interface;
 receive instructions from the remote server and translate said instructions into control signals for the haptic actuators;
 receive 3D map of a location associated with the skier GPS coordinates from a remote server; and
based on bio-mechanics of skiing and the skis' trajectory and the second information, estimate future skis' trajectory then provide haptic instruction of time the COP location must be changed, display location numerical and graphical information of location and distribution of the COP and COF in relation to skis' pitch, roll and heading and overlay said information on the 3D map on the smart-phone screen.

2. The system of claim 1, wherein motion and force processing element comprises:
 a three-axis accelerometer;
 a three-axis gyroscope;
 a three-axis magnetometer; and
 a multiplicity of force pressure sensors;
and wherein said motion and force processing element is configured to measure motion vectors in relation to location of COP and timing the COP and COF is changed and to communicate said changes to a smart-phone based application.

3. A system for processing of location and timing of change of Center of Pressure (COP) and distribution of Center of Force (COF) to a skier's ski boots during a ski run and the skier's location GPS coordinates are processed by a remote server to provide a visual and numerical representation of each turn, and wherein said GPS coordinates are used to generate a 3D map of the area and wherein said 3D map is sent to the skier's smart-phone or wherein said 3D map and the location and timing of change of COP and the distribution of COF and location of COM is stored in a remote server.

4. The system of claim 3, wherein visual and numerical representation of each turn and a 3D map can be retrieved from remote server by user of a smart-phone for visualization and analysis.

5. The system of claim 3, wherein visual and numerical representation of each turn and a 3D map can be retrieved from a remote server by an instructor and used as reference to provide instructions and to send said instructions to user's smart-phone over the smart-phone cellular radio interface and wherein said instructions are translated into control signals by the smart-phone based analysis application before being applied to haptic actuators.

6. The system of claim 3, wherein location of Center of Pressure (COP) an timing of change in location of COP and distribution of Center of Force (COF) applied to ski boot insoles are collected independently and sorted according to velocity into turn radius sets for left and right turn respectively and wherein the results of same velocity set for left turn is compared to the same velocity set for the right turn and wherein the difference in results is displayed as symmetry of COF distribution.

7. A method for analysis of changes in location of Center of Pressure (COP), and location and distribution of Center of Force (COF) transmitted to ski boot insoles, and to provide instructions of timing, the location of COP must be applied for successful termination of turn, wherein said method comprises:
 estimating skis current trajectory and phase of turn by sampling the motion and rotational vectors;
 estimating the location of COP and the distribution of COF in relation to the motion and rotational vectors;
 estimating skier's Center of Mass (COM) by analyzing current ski trajectory, location of COP and COF in relation to skier kinematic model;
 estimating skis future trajectory by analyzing the phase of turn, the motion and rotational vectors and the location of COP and the distribution of COF in relation to skiing bio-mechanical model;
 instructing on the timing when the location of COP must be changed; and
displaying numerical results of said analysis, and wherein said numerical results are overlaid on 3D map generated form GPS coordinates obtained during the ski run and wherein said numerical and visual results are displayed on a selected user smart-phone or on a dedicated remote terminal.

8. The method of claim 7, wherein instructions related to location of force necessary for successful termination of ski turn is obtained by analyzing orientation of selected user's feet, ski velocity and trajectory, equipment parameters and the selected user physical parameters.

9. A non-transitory computer accessible memory medium for storing program instructions pertaining to a system to analyze motion and balance of a skier by analyzing changes in location of Center of Pressure (COP), and changes in location and distribution of Center of Force (COF) applied to ski boot insoles, and using said analysis to provide estimation of location of the skier's Center of Mass (COM), and an estimation of past and future ski trajectories, and to provide instructions to the skier on location the COP must be applied for successful termination of a current turn and to obtain optimal position for next turn, wherein the program instructions execute all of the following:
 maintaining communication with a motion and force processing element embedded in the ski boot insoles and with a remote server;
 obtaining system's global and local coordinates by analyzing data obtained from motion processing element;
 obtaining skis' current trajectory and phase of turn by integrating motion and rotational vectors received form the motion processing element;
 obtaining location of Center of Pressure (COP), by monitoring timing and values recorded by the motion and force processing element;
 obtaining location and distribution of COF by monitoring timing of change in the location of COP in relation to motion vectors;
 obtaining location of Center of Mass (COM), by monitoring the location and distribution of COF in relation to the skier's body kinematic model;
 obtaining skis future trajectory by applying ski technical parameters data and the skis' current trajectory, and the location of COP and COF to skiing bio-mechanical model;

providing instructions about location the COP must be applied and timing of said application which is required for successful termination of turn by applying control signals to haptic actuators embedded in the ski boot insoles;

obtaining the skier location GPS coordinates;

transmitting motion and force vectors and location GPS coordinate data to a remote server and receiving instructions and 3D maps from the remote server using smart-phone cellular radio interface;

receiving instructions from a remote and applying said instructions as control signals to the haptic actuators embedded in the ski boot insoles;

performing calibration procedures to obtain reference values of force during static and dynamic test conditions;

estimating skis' current trajectory and phase of turn by sampling the motion and rotational vectors;

estimating the location of COP and the distribution of COF in relation to the motion and rotational vectors;

estimating skiers Center of Mass (COM) by analyzing current ski trajectory, location of COP and COF in relation to skier's kinematic model;

estimating skis' future trajectory by analyzing the phase of turn, the motion and rotational vectors and the location of COP and the distribution of COF in relation to skiing bio-mechanical model;

instructing on the timing the location of COP must be changed; and providing visual and numerical results of skis' pitch, roll and heading in relation to changes in location and distribution of COP and COF applied by feet to the ski boot insoles.

10. The system of claim 1, wherein first information stored in smart-phone based analysis application comprises of: a skier's weight and height; distance between the skier's ankle and knee and the distance the skier's knee and hip, and wherein said information is used to generate the skier's kinematic mode.

11. The system of claim 1, wherein the second information stored in smart-phone based analysis application contains information related to ski parameters and comprises of: ski length and weight and skis' side-cut characteristics, and wherein said parameters and motion and rotational vectors and bio-mechanical model of skiing is used to estimate skis' trajectory.

12. The system of claim 1, wherein skier's COM is obtained by applying the location of COP and COF and the motion and rotational vectors to the skier's kinematic model.

13. The system of claim 1, wherein past skis' trajectory and current phase of turn is obtained by integrating samples of motion and rotational vectors in the analyzer memory then applying said representation of skis' trajectory to model of skiing bio-mechanics.

14. The system of claim 1, wherein future skis' trajectory is obtained by analyzing location of COP and distribution of COF in relation past skis' trajectory, current phase of turn and second information containing skis' physical parameters.

15. The system of claim 1, wherein results of analysis can be retrieved for smart-phone memory and displayed numerically graphically on the smart-phone User Interface (UI) screen and wherein said numerical and graphical data provides visualization of skis' pitch, roll, heading and turn radius in relation to changes in location and value of COP and distribution of COF.

16. The system of claim 1, wherein location 3D map is generated by a remote server from information received in third information and wherein said 3D map of location is transmitted to smart-phone.

17. The system of claim 16, wherein smart-phone based analysis application synchronizes motion and rotational vectors and a location of COP, location and distribution of COF, skis' trajectory and turn phase, and location to 3D map received from remote server and displays said data on the smart-phone User Interface (UI).

* * * * *